United States Patent [19]
Kanamori et al.

[11] Patent Number: 5,588,555
[45] Date of Patent: Dec. 31, 1996

[54] SYNTHETIC APPARATUS FOR INSPECTION OF BLOOD

[75] Inventors: Shigeo Kanamori, Mikishi; Kensaku Aota, Hyogoken; Takashi Demachi, Tarumiku; Takahiro Inoue, Himejishi; Kiyoyuki Tanaka, Onoshi, all of Japan

[73] Assignee: TOA Medical Electronics Co., Ltd., Kobe, Japan

[21] Appl. No.: 302,543

[22] Filed: Sep. 8, 1994

Related U.S. Application Data

[62] Division of Ser. No. 975,407, Nov. 12, 1992, Pat. No. 5,356,595, which is a division of Ser. No. 865,344, Apr. 8, 1992, Pat. No. 5,270,012, which is a division of Ser. No. 577,689, Sep. 4, 1990, Pat. No. 5,209,903.

[30] Foreign Application Priority Data

| Sep. 6, 1989 | [JP] | Japan | 1-230675 |
| Oct. 6, 1989 | [JP] | Japan | 1-118146 |
| Jun. 13, 1990 | [JP] | Japan | 2-62283 |
| Jun. 13, 1990 | [JP] | Japan | 2-62284 |
| Jun. 13, 1990 | [JP] | Japan | 2-62285 |
| Jun. 13, 1990 | [JP] | Japan | 2-62286 |
| Jun. 13, 1990 | [JP] | Japan | 2-62287 |

[51] Int. Cl.$^6$ .................................................. B65H 1/00
[52] U.S. Cl. ........................................................ 221/197
[58] Field of Search ............................ 221/197, 287, 221/282

[56] References Cited

U.S. PATENT DOCUMENTS

| 3,163,327 | 12/1964 | Maxwell | 221/197 |
| 4,299,333 | 11/1981 | Welsch | 221/197 |

*Primary Examiner*—Kenneth Noland
*Attorney, Agent, or Firm*—Morrison Law Firm

[57] ABSTRACT

A blood analyzer system transports blood samples through at least one blood analyzer and an automatic blood smear generator under the control of a preprogrammable controller. Blood samples are stored in containers that identify the blood samples they contain. The containers move through the system mounted in protective racks that permit the reading of the identifications. The results of analysis by one or more blood analyzers in the system determines for each sample individually whether or not to make a blood smear. When a blood smear is to be made, the controller makes the smear thickness of each blood sample consistent with other samples whatever the consistency of the sample to be smeared. If a required sample is not made, a detector sounds an alarm, thereby alerting operators that the system has failed.

8 Claims, 24 Drawing Sheets

SYNTHETIC APPARATUS FOR INSPECTION OF BLOOD

This application is a divisional of application Ser. No. 07/975,407, filed Nov. 12, 1992, now passed to issue now U.S. Pat. No. 5,356,595, which was a divisional of application Ser. No. 07/865,344, filed Apr. 8, 1992, and issued as U.S. Pat. No. 5,270,012 on Dec. 14, 1993, which was in turn a divisional of application Ser. No. 07/577,689 filed Sep. 4, 1990, and issued as U.S. Pat. No. 5,209,903 on May 11, 1993.

BACKGROUND OF THE INVENTION

The present invention relates to a general blood analyzing system and more particularly to an integrated general blood analyzing system that comprises a sample (sample)-rack transportation system, blood analyzers, and an automatic smearing device.

Blood analyzers which take blood samples from a sample container and then-classify and count blood corpuscles are well known, as are devices that make a smear sample by smearing the blood sample on a slide glass.

Japanese Patent Laid-open Publication No. 63-217273 discloses a system that combines more than one blood analyzer for the performance of a variety of tests with a transportation device for an array of blood samples in sample containers. However, this system does not include the preparation of blood smears for further examination, requiring that the blood smears be made by hand or that the samples be transferred to other devices for the preparation of smears.

Automatic smearing devices for preparing blood smears on slides are also well known. Japanese Patent Laid-open Publications No. 61-45769, No. 62-16380, and No. 57-171259 disclose automatic apparatus for preparing blood smears. Publication No. 61-45769, describes an apparatus, wherein at least one of a moving velocity and an angle of a pulled glass is varied continuously as it is drawn over a blood specimen in order to make the thickness of a sample blood smear constant. Publication No. 62-16380 describes an apparatus wherein the rotating speed of a motor is controlled in order to disperse blood corpuscles evenly on a slide glass. Publication No. 57-171259, describes an apparatus wherein the angle of a pulled glass decreases gradually as it is drawn over a blood specimen so as to minimize the changes in smear thickness.

In the spinner method, a drop of blood is placed on the surface of a glass slide, which then is spun so that the blood is spread over the surface and smeared by centrifugal force. The wedge method, on the other hand, is a method in which a glass slide is drawn through a blood sample along its long side to smear blood on its surface.

However, these methods do not provide consistency between smear samples because they do not adjust for variations in specific character between blood samples.

A smeared sample rack is provided into which smeared slides are placed. The smeared samples are then dipped in a dyeing liquid along with the smeared sample rack.

The smeared sample rack needs a handle with which it can be carried or dipped into a dyeing liquid. When the rack is held by its handle, the handle must be centered. However, in an automatic loading device the rack handle must be movable so as not to interfere with loading of the rack. In addition, the handle must always take the same position each time the rack is loaded to facilitate the handling of loaded racks. Conventional racks do not meet these requirements.

For quality analysis, the thickness of prepared blood smears must be consistent from smear to smear, regardless of the great variety of possible blood consistencies.

Japanese Examined Patent Publication No. 61-45769 discloses a method to achieve the required consistency in which at least one of the angle or the velocity of a smearing glass is changed continuously. However, this device cannot automatically determine the consistency of the blood to be smeared and must be adjusted for separate blood samples.

Separate devices for measuring blood viscosity are well known. For example, a method is known that determines blood viscosity by measuring its flow time through a measured length of capillary tubing. It is not clear how these conventional devices could be installed in an automatic smearing device. If such a blood viscosity measuring device were integrated into an automatic smearing device, the device would be complex, large, slow and costly.

Although an automatic smearing device employs automated smearing preparation processes, various monitoring functions are required. Detection of the presence of a smear is an example. If there is no blood smear on a slide to be examined because of a machine malfunction, a warning must be issued.

A conventional method for detecting a blood smear focuses a known intensity light through a smeared slide and measures the intensity of the light transmitted by the slide. The light loss through a blood smeared slide is greater than that through a clean slide. However, because of the variety of smears produced, a very thin smear might not be detected.

Conventional methods for printing an identifier on a blood smeared slide include a printer disclosed in Japanese Examined Patent Publication No. 55-48655 that uses a printing plate and ink.

The major problem presented by the use of a printing plate and ink is that because the smeared specimen is dyed following blood sample smearing and the dyeing liquid contains alcohol, identifying marks imprinted in ink may wash off during the dyeing process.

Another approach is to imprint the identifier with a thermal printer on a resin-coated portion of a slide. This method requires that expensive, specially prepared slides be used for preparing smeared blood samples.

The use of a dot matrix impact printer for imprinting identifiers on slides is also well known. Dot matrix impact printers print using a printer head that strikes an ink ribbon with pins of a printer head to leave ink dots on the slide being identified.

Problems that limit the effectiveness of conventional dot matrix impact printers include the breaking of slides as they are impacted by printer head pins and the short life of the printer head pins when used in this application.

Another major problem of conventional dot matrix impact printers is that they do not provide good penetration of ink into the hollows of the ground glass portion of the slides on which the printing is done. This allows the ink identifier to be washed away during dyeing.

OBJECTS AND SUMMARY OF THE INVENTION

Accordingly, it is an object of the invention to provide a blood analyzer system that overcomes the drawbacks of the prior art.

It is a further object of the invention to provide a blood analyzer system incorporating a fully integrated smear generator for making blood smears automatically as required.

It is a still further object of the invention to provide a smear generator that automatically adjusts to the thickness of the various blood samples to make smears of consistent thickness.

It is a still further object of the invention to provide improved means for the convenient and safe handling of blood samples.

Briefly stated, the present invention provides a blood analyzer system that incorporates means for handling and transporting sample blood through at least 1 blood analyzer and an automatic blood smear generator under the control of a programmable controller. Blood samples are stored in sample containers having identifiers for the sample blood that they contain. These sample containers are transported through the system in protective racks that permit the reading of the identifiers. The results of analysis by one or more blood analyzers in the system determine the need for performing or omitting subsequent operations on a particular sample blood. When a smeared blood sample is to be made, the controller assures that the smear thickness is consistent with other samples regardless or the thickness or viscosity of the sample blood. If the system fails to make a required smeared blood sample, a detector sounds an alarm, warning of a system failure.

According to an embodiment of the invention, there is provided apparatus for automatic processing of blood, comprising: at least one blood analyzer for analyzing a sample blood, at least a second blood processing device, and means for actuating the second blood processing device in response to a result from the at least one blood analyzer.

According to a feature of the invention, there is provided an automated handling device for handling sample containers, comprising: the sample containers including identifying markings thereon, a conveyor, a sample rack movable on the conveyor for containing at least one of the sample containers, a reader effective for reading the identifying markings, and means for rotating the at least one sample container about an axis effective to bring the identifying markings into a position readable by the reader.

According to a further feature of the invention, there is provided an automated smear generator comprising: a conveyor, means for delivering at least one slide to the conveyor, at least first and second positions along the conveyor, means at the first position for depositing a blood drop on the at least one slide, means at the second position for smearing the drop of blood to produce a smeared blood sample, and means for unloading the at least one slide from the conveyor.

According to a still further feature of the invention, there is provided apparatus for printing information on a glass slide, the glass slide including a frosted area, comprising: the frosted area including a plurality of projections, an impact printer, the impact printer including an impacting element, an ink carrier between the impacting element and the frosted area, and the impacting dement being effective to strike the ink carrier with sufficient force to at least partly crush a substantial number of the plurality of projections, whereby the ink is transferred to the frosted area in a pattern determined by the impacting element.

According to a still further feature of the invention, there is provided a smear detector for detecting a smeared blood sample on a slide, comprising: a light source, a light detector, a light beam passing from the light source to the light detector along an axis, the axis being inclined at an angle to a surface of the slide, and the angle being from about 30 to about 75 degrees.

According to a still further feature of the invention, there is provided a slide supply device comprising: means for accepting at least one rack containing a plurality of slides, a slide outlet port in the rack, closing means effective to prevent the slides passing through the outlet port, and cooperating means between the rack and the means for accepting for moving the closing means to a position permitting the slides to pass through the outlet port.

According to a still further feature of the invention, there is provided apparatus for detecting the presence of a slide, the slide including a frosted area comprising: a light source projectable on the frosted area when a slide is present, a light detector effective for detecting light reflected from the frosted area when the slide is present, and the light detector being in an alarm condition when a slide is not present.

According to still another feature of the invention, there is provided apparatus comprising: a rack for holding a stack of slides, each of the slides including a frosted area thereon, a light source projectable on the frosted area when a slide is present in the rack, a light detector effective for detecting light reflected from the frosted area when the slide is present, and the light detector detecting that the rack is empty when a slide is not present.

According to yet another feature of the invention, there is provided a blood preparation system comprising: means for drawing a sample of blood through a tube, means for measuring a time for blood to flow through a predetermined length of the tube to produce a measured time, and means for using the measured time to control subsequent operations on the sample of blood.

According to a still further feature of the invention, there is provided a smearing fixture for smearing a sample blood comprising: a glass holder, the glass holder including means for holding a smearing glass, a pivotable support for the glass holder, resilient means for urging the smearing glass into contact with a surface of a slide, the contact being at an angle with respect to the surface, and means for moving the smearing fixture up and down whereby the angle may be varied.

According to a still further feature of the invention, there is provided a smeared sample rack comprising: a rack body, a handle, cooperating means in the handle and the rack body for pivotably mounting the handle to the cassette body, the cooperating means permitting first and second positions for the handle, the first position being substantially vertical, and the second position being inclined at an angle from the vertical.

The above, and other objects, features and advantages of the present invention will become apparent from the following description read in conjunction with the accompanying drawings, in which like reference numerals designate the same elements.

DETAILED DESCRIPTION OF PREFERRED EMBODIMENTS

Figure 1:
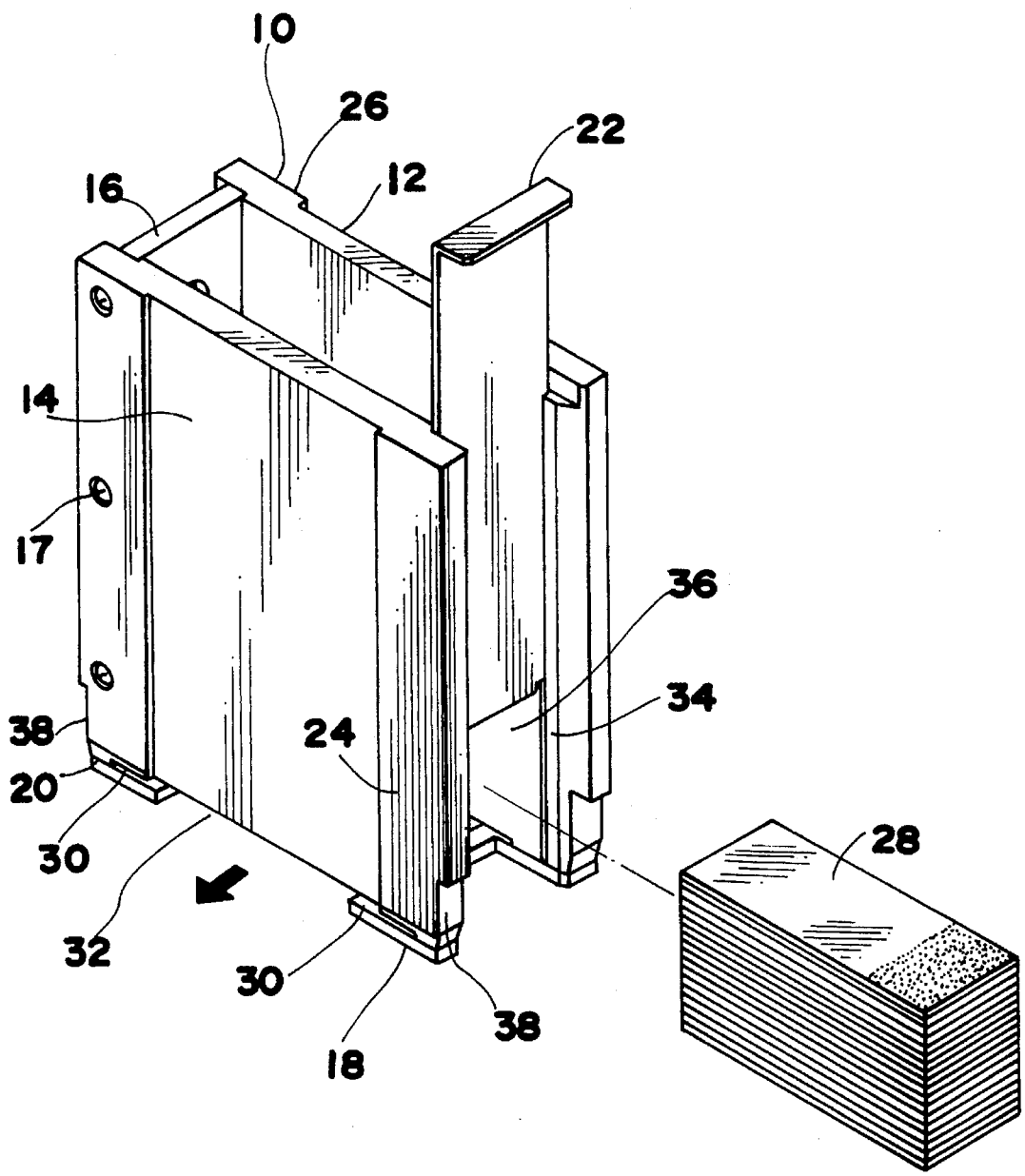
FIG. 1 is a perspective view of a conventional slide rack.

Referring to FIG. 1, there is shown a cassette 10 of the prior art. Cassette 10 is a rectangular tube that comprises a fight side wall 12, a left side wall 14 spaced apart by a rear wall 16 secured by screws 17. A sliding front wall 22 closes a front of cassette 10. A front bottom wall section 18 is disposed across a forward end of a bottom opening of cassette 10, while a rear bottom wall section 20 is disposed across a rear end of the bottom opening, so as to define a broad opening of the bottom of cassette 10 between them. Front bottom wall section is U-shaped leaving an open space at the front bottom of cassette 10.

Front and rear thickened edges 24 and 26, respectively, of left and right side walls 12 and 14 are thickened for increased rigidity and project downwardly slightly more than the thickness of a slide to form notches 30 with front and rear bottom wall sections 18 and 20. Notches 30, together with the bottom of cassette 10, forms an outlet port 32.

Sliding front wall 22 is supported in opposing grooves 34 on the inner facing surfaces of front thickened edges 24 so as to be slidable up and down to cover opening 36. Recessed notches 38 at the bottom fronts of front thickened edge 24 and the bottom rear of thickened edge 26 stabilize an installed cassette 10.

Cassette 10 is loaded by raising sliding front wall 22 and inserting a stack of slides 28 into cassette 10 through opening 36. During operation, slides are taken one at a time through outlet port 32 in the direction of the arrow.

Cassette 10 has capacity of about 100 slides 28. Because slides 28 have highly polished surfaces, they tend to bind. When cassette 10 is nearly full, the weight of stacked slides 28 causes the bottom most slide 28 to resist being removed through outlet port 32.

On the other hand, when there are only a few slides in cassette 10 the bottommost slide 28 tends to fall out of cassette 10 through slide outlet port 32 whenever cassette 10 is tilted. This makes it awkward to handle cassette 10.

Figure 2:
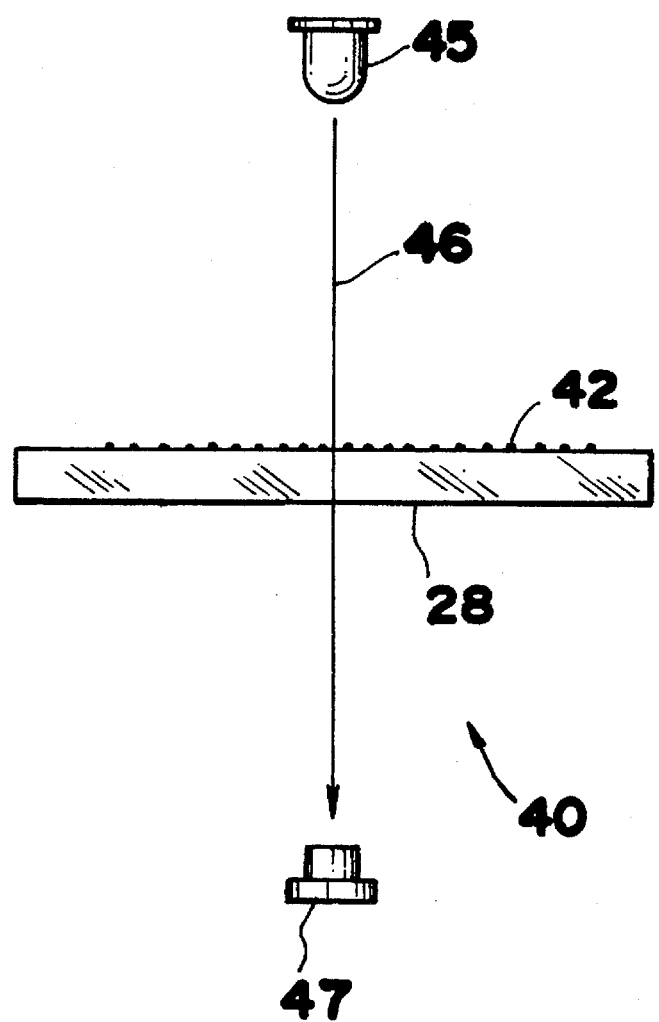
FIG. 2 is a side view of a conventional smear detector.

Referring to FIG. 2 there is shown a blood smear detector 40 of the prior art. Slide 28 has a blood smear 42 on a surface facing light emitter 45. Light emitter 45 emits a light beam 46 toward the surface of slide 28. On the side of slide 28 opposite light emitter 45 a light detector 47 is positioned to form a path for light beam 46 between light emitter 45 and light detector 47 that is approximately perpendicular to a surface of slide 28.

Figure 4:
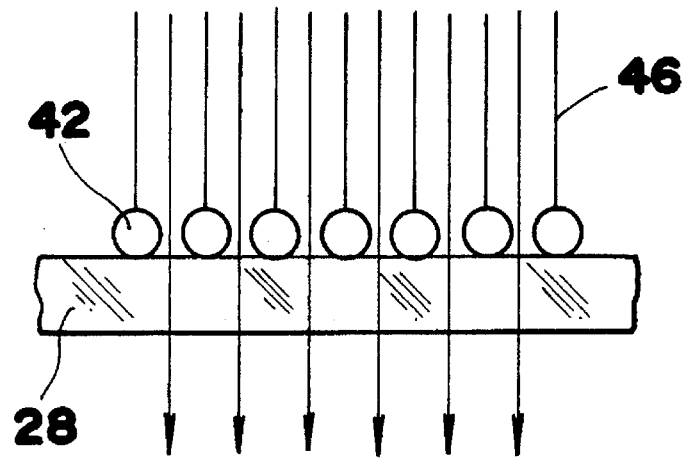
FIG. 4 is a magnified view of FIG. 2 showing blood particle distribution on a slide with a thin smear.

During smear detection, when the blood smear is thin (as shown in FIG. 4), light beam 46, transmitted through a blood smeared slide 28, is almost as intense as light beam 46 transmitted through a clean slide. As a result, a very thin blood smear 42 may not be detected.

Figure 3:
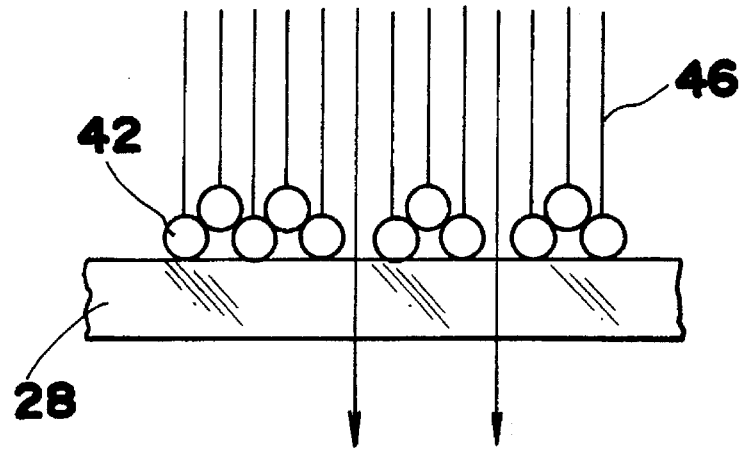
FIG. 3 is a magnified view of FIG. 2 showing blood particle distribution on a slide with a thick smear.

When blood smear 42 is thick (as shown in FIG. 3) blood smeared slide 28 transmits much less light than a clean slide 28 making the detection of blood smear 42 certain. The prior art described herein is unacceptable, because this device is able to detect only relatively thick blood smears 42.

Figure 5:
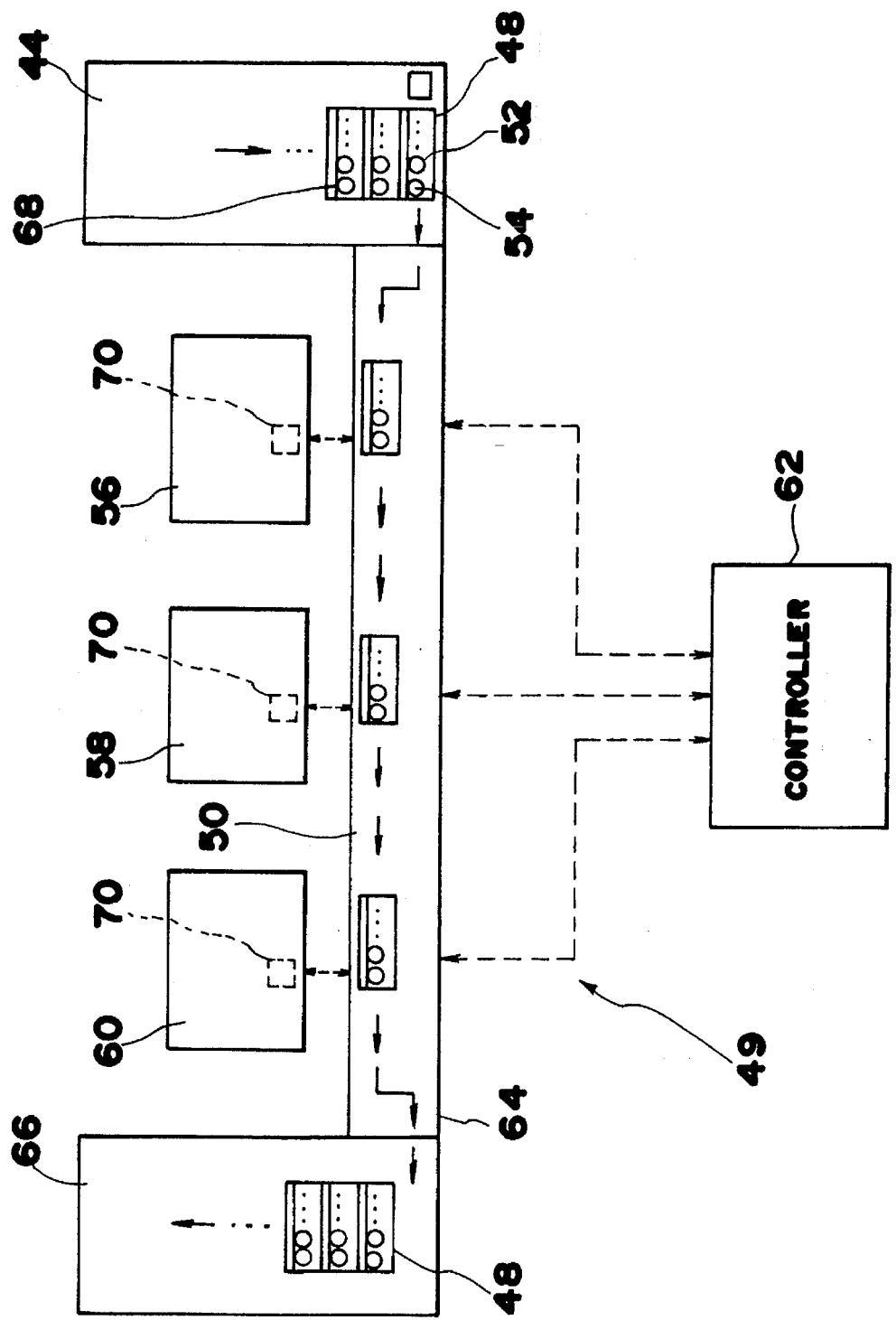
FIG. 5 is a system plan view of an embodiment of the invention.

Referring to FIG. 5, an unloader 44 of a blood analyzer system 49 is loaded with a plurality of sample racks 48 to be unloaded onto an entry end of a conveyor 50 that is in a position proximal to unloader 44. Each sample rack 48 contains a plurality of sample containers 52, which may be test tubes or the like, each filled with a blood sample for analysis.

The contents of sample container 52 can be analyzed with or without a rubber stopper 54 in its opening. In either case, a blood sample in the sample container 52 is drawn using conventional means.

Conveyor 50 transports sample racks 48 through at least one of a blood corpuscle analyzer 56, a reticulate red blood corpuscle analyzer 58, and a smear generator 60. Other devices may be employed with the above devices without departing from the spirit of the invention. All of the operations performed by the invention are controlled by a controller 62, which continually monitors the process.

Following the last blood analysis device, sample racks 48 reach a discharge end 64 of conveyor 50, where a loader 66, disposed at the discharge end 64 of conveyor 50 loads sample racks 48 for removal.

A sample rack 48 carries more than one sample container 52. Each sample container 52 has an identifying bar code label (not shown) that can be read from the outside of sample rack 48. Each sample rack 48 includes a bar code access window 68 on its side for each sample container 52 it can hold. Bar code readers 70, located at each process position, view the bar codes through the bar code access windows 68. Japanese Patent Laid-open Publication 63-217273 discloses an example of this.

Sample containers 52 are placed in sample racks 48 in generally random rotational orientations. Thus, a bar code on a sample container 52 may not be turned to face its bar code access window 68. To assure that the bar code label on sample containers 52 is properly read at each process position, sample containers 52 are rotated within sample rack 48 by a rotator 71 shown in FIG. 6.

Figure 6:
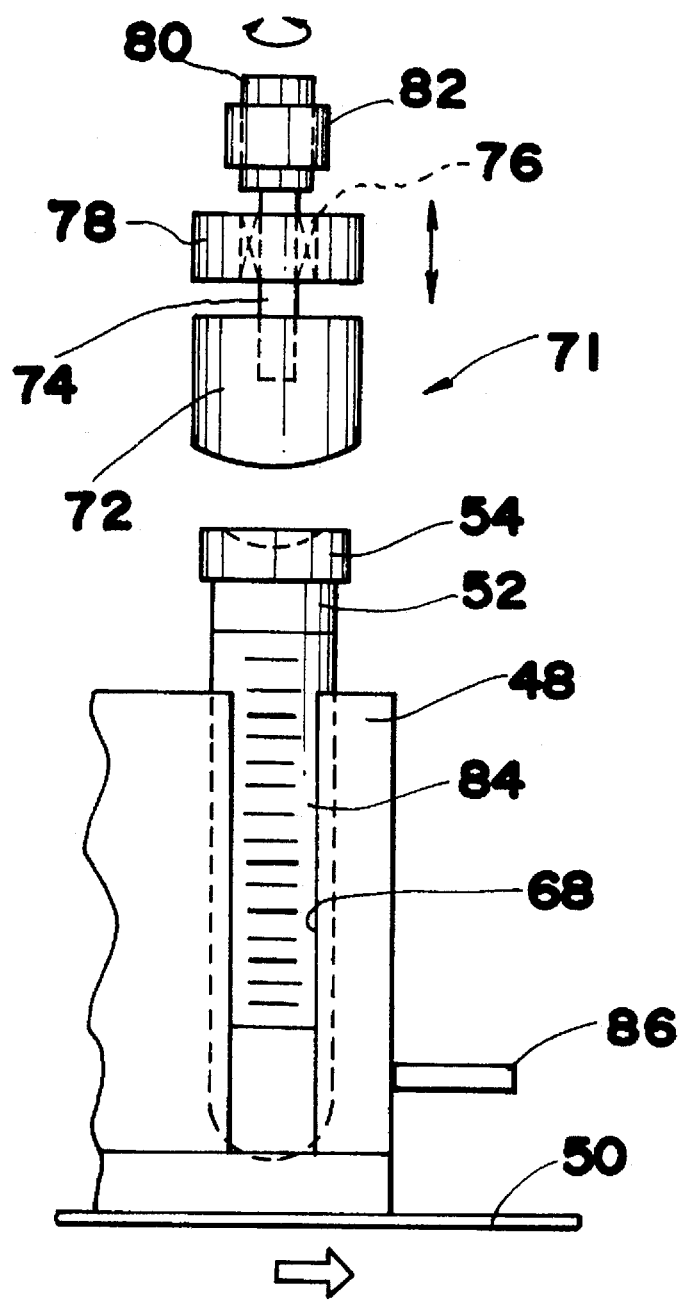
FIG. 6 is a side view of a rotating means for the sample containers shown in FIG. 5.

Referring to FIG. 6, a robber cylinder 72 of rotator 70 is axially suspended from a shaft 74. Shaft 74 is rotatably supported by a bearing 76 in a support 78. A pulley 80 on shaft 74 is rotated by a motor (not illustrated) through a belt 82, causing rotation of rubber cylinder 72. Rotator 71 is moveable up and down with assistance of another driving source (not illustrated) to engage and release a rounded bottom of rubber cylinder 72 with rubber stopper 54 of sample container 52.

Rotator 71 is lowered to engage rubber cylinder 72 with rubber cap 54. Rubber cylinder 72 is also rotated slowly, thus slowly rotating sample container 52. As sample container 52 rotates, a bar code 84 can be read regardless of the initial orientation of sample container 54. A stop 86 at each processing location holds sample rack 48 in a fixed position on conveyor 50 until the process step at that location is completed.

Figure 7:
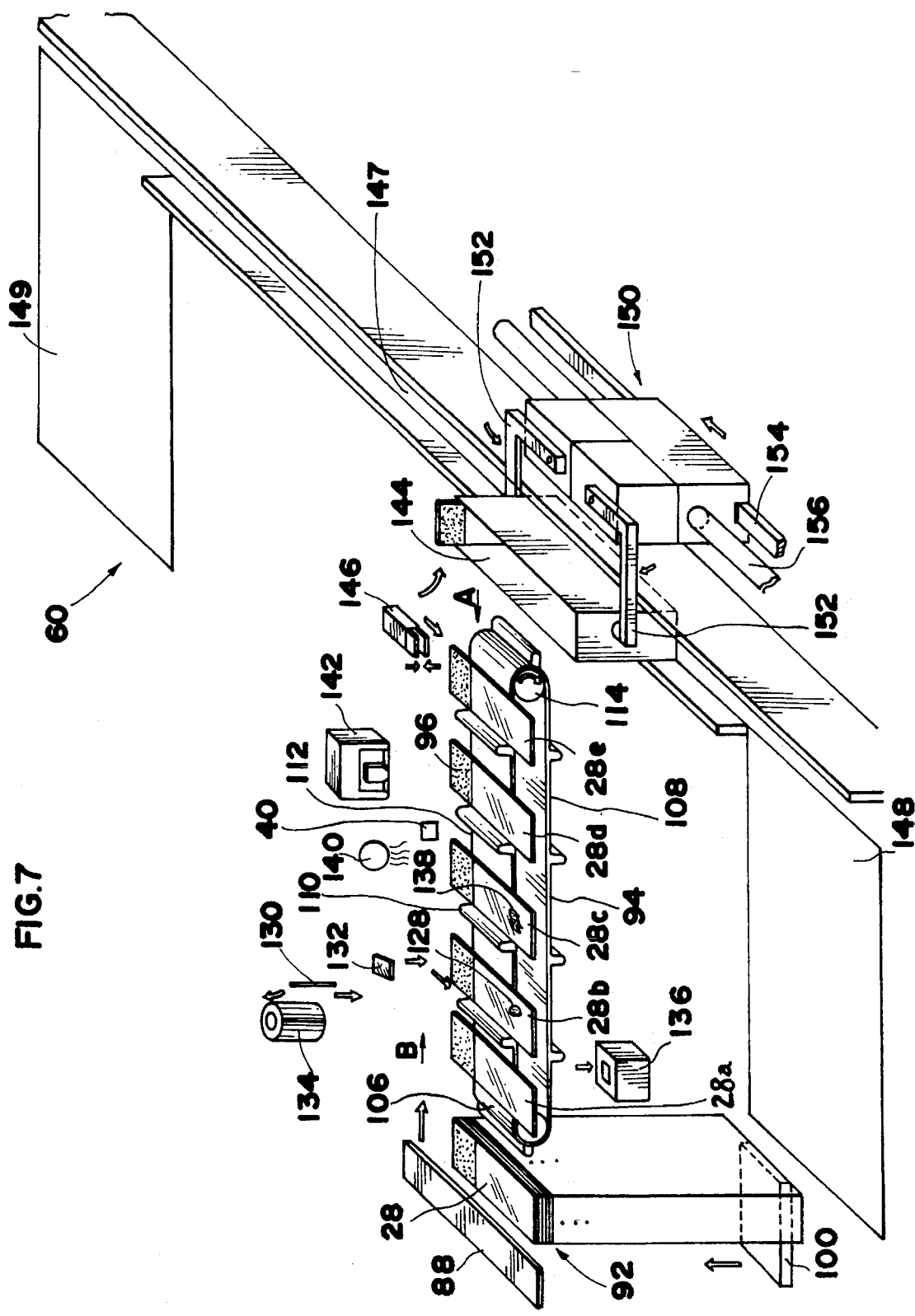
FIG. 7 is a perspective view of the smear generator.

Referring to FIG. 7, supplier 88 of smear generator 60 supplies one slide 28 at a time from the top of a slide stack 92 to a slide conveyor 94. Slide 28 may be 76 mm×26 mm×0.9 ½ mm in size and have a frosted area 96 on which an identifier may be printed.

With slide stack 92 in place, a stack lifter 100 lifts slide stack 92. Supplier 88 shifts to the right to push a topmost slide 28 onto an entry end 106 of a conveyor 104. Conveyor 104 steps slides 28 one after another to each stage of blood smear generation on an endless conveyor belt 108. Conveyor belt 108 has a plurality of protrusions 110 that define spaces 112 between them for transporting slides 28. A roller 114, disposed at each end of conveyor 104, both supports and drives conveyor belt 108.

Figure 8:
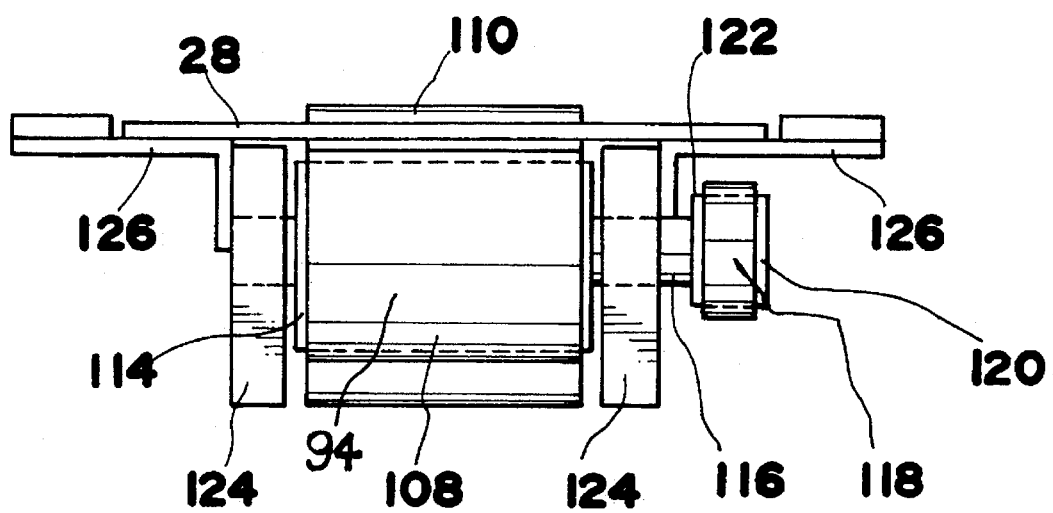
FIG. 8 is an end view of the conveyor belt as seen from arrow A in FIG. 7.

Referring now to FIG. 8, there is shown a view of conveyor 104 as seen in the direction of arrow A of FIG. 7. Roller 114 is rotatably supported by a shaft I 16, axially attached to an end 122 of roller 114. A pulley 120 is affixed to the end of shaft 116. A timing belt 118 is driven discontinuously (by conventional means not shown) to step conveyor belt 108 one slide space at a time. Disk shaped plates 124 are axially supported by shaft 116 so that they support opposite edges of conveyor belt 108. Supporting plates 126, disposed on opposite sides along the entire length of conveyor belt 108, support ends of slides 28, as they are pushed along by protrusions 110.

Referring again to FIG. 7, major blood smear generation devices, to be described below, are disposed along conveyor 104. In the illustration, five slides 28a through 28e are shown in place on conveyor 104 for processing by these devices. Slide 28a, positioned at the left end of conveyor 104 is in a waiting position. Slide 28b is in a position receiving sample blood drops 128 from a dropper 130. A smearing glass 132 smears blood drops 128 on slide 28b, to produce a smeared blood sample 138, as will be described.

A dropper washer 134 and a smearing glass washer 136 are located proximal to dropper 130 and smearing glass 132, respectively, to wash them between the preparation of smeared blood samples.

Smeared blood sample 138 on slide 28c is dried by a fan 140. Slide 28d is imprinted with an identifier by a printer 142 on frosted area 96, while slide 28e, with smeared blood sample 138 and identifier imprint thereon is loaded into a smeared sample rack 144 by a mechanical hand 146.

Smeared sample rack 144 is moved between loading platform 148 and an unloading platform 149 on a track 147 by a hold and move means 150. Hold and move means 150 holds smeared sample rack 144 using arms 152. Hold and move means 150 is moved along track 147 on a guide 154 positioned parallel to track 147 by any conventional device such as, for example, a lead screw 156. A conventional drive means (not shown) operates lead screw 156.

Figure 9:
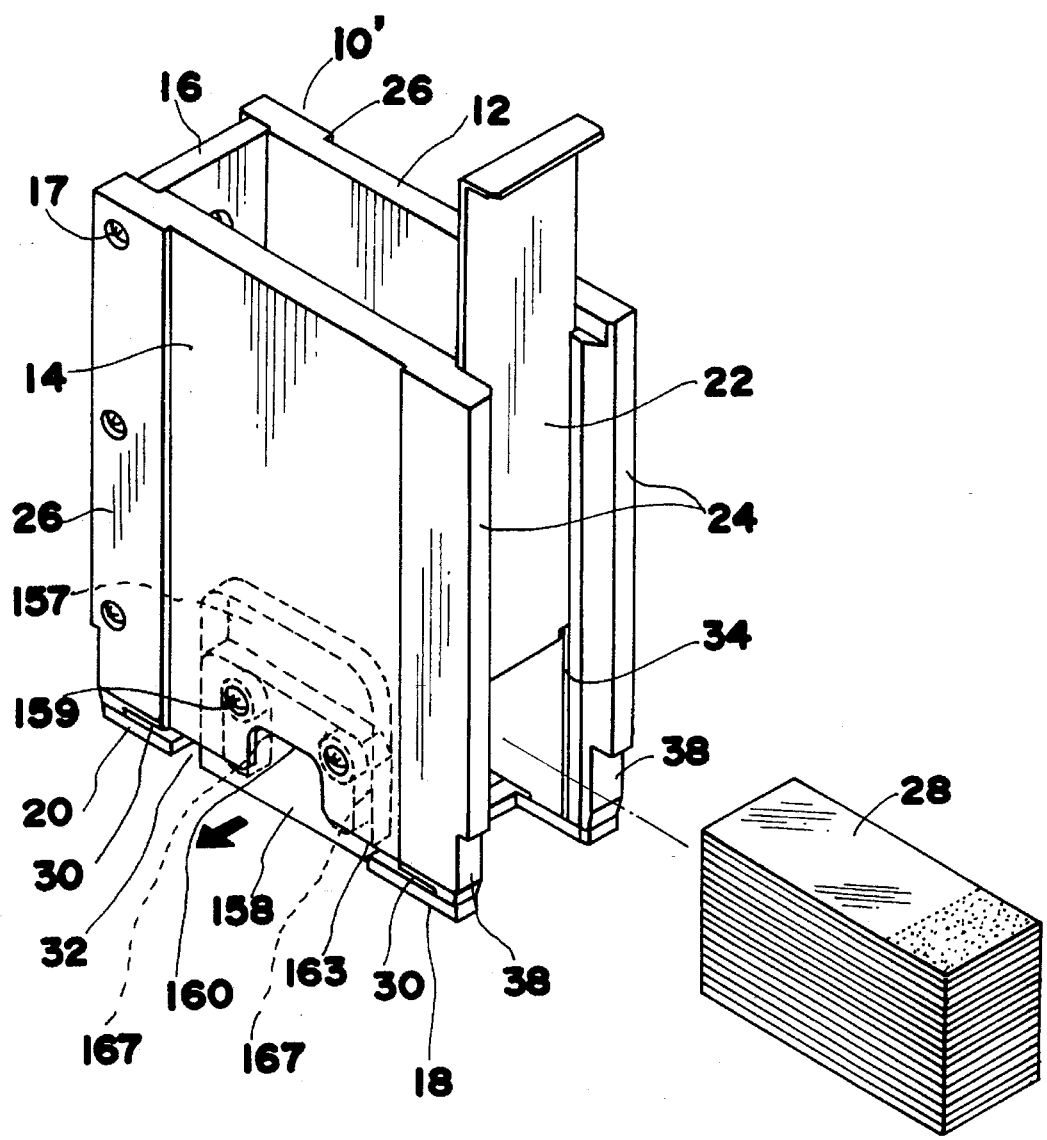
FIG. 9 is a perspective view of an embodiment of the slide cassette according to the invention.

Referring to FIG. 9, a cassette 10', according to the present invention, is the same as the prior art cassette 10 shown in FIG. 1, and described in the foregoing except for differences recited in the following paragraphs. Parts of cassette 10' that are the same, and have the same functions, as previously described are not described again.

A left side wall 14' includes a recess 157. A shutter 158 is disposed in recess 157. Recess 157 is deeper than the thickness of shutter 158 so that shutter 158 can move smoothly within it. Two props 159, vertically positioned at the forward and rearward edges of recess 157, slidably support and allow up and down motion of shutter 198.

A deep cutaway 160 above slide outlet port 32 allows a contactor 161 (shown in FIG. 10) of a turntable 162, to be described later, to raise shutter 158. Shutter 158 opens and closes outlet port 32. Shutter 158 must be fully opened to allow a slide 28 to be removed from cassette 10. In this embodiment, shutter 158 moves up and down on tracks 163 to open and close slide outlet port 32.

As would be clear to one skilled in the art, shutter 158 may move from side to side or be hinged without departing from the present invention.

Shutter 158 is normally moved to the closed position by its own weight to cover outlet port 32, thus preventing the bottommost slide 28 from sliding out of cassette 10 when carried. When shutter 158 is moved up from the bottom along tracks 163, formed between left side wall 14' and props 159, slides 28 can be slid out of outlet port 32 one at a time.

Figure 10:
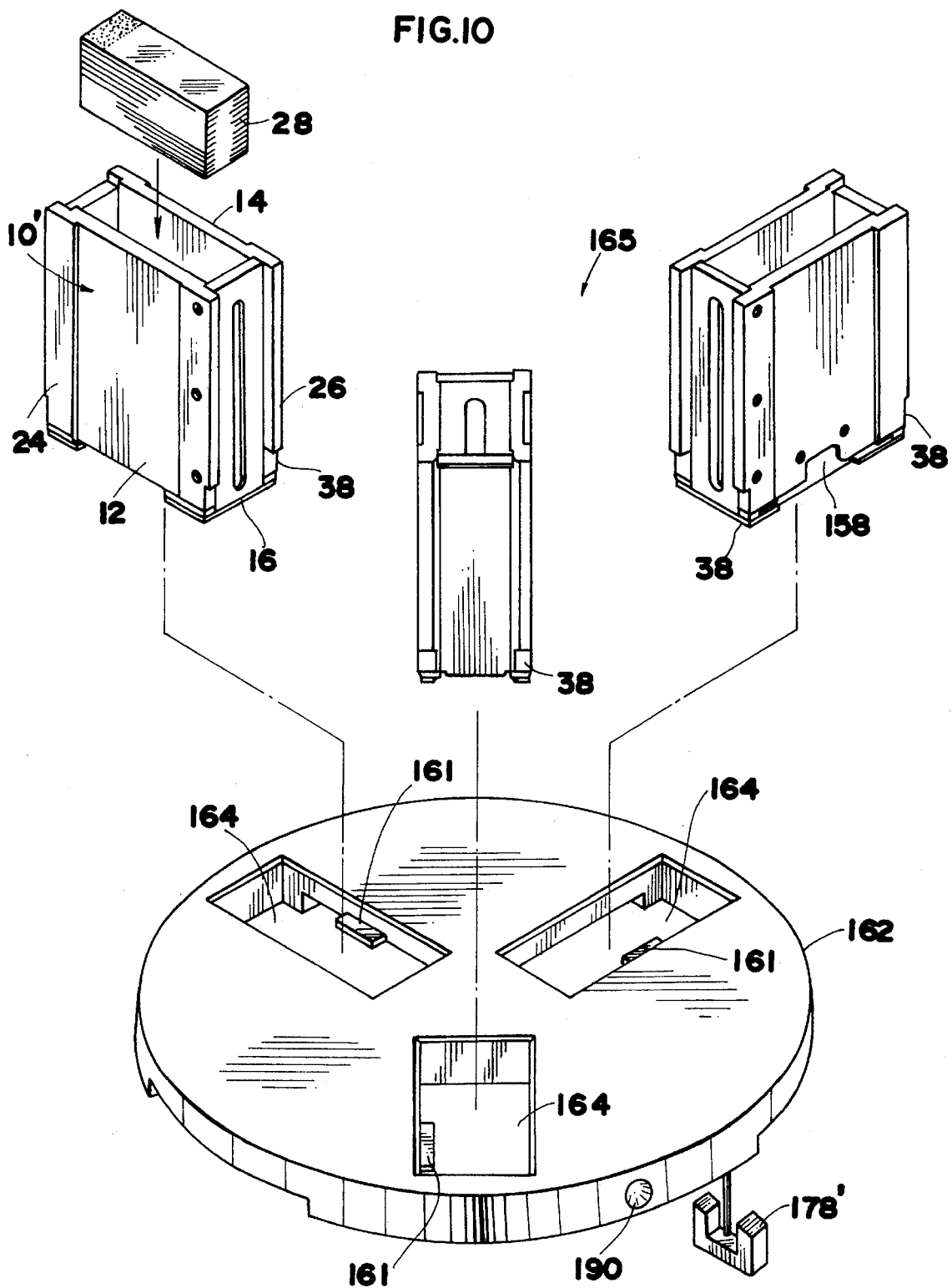
FIG. 10 is a perspective view of the slide supplying turntable.

Referring to FIG. 10, turntable 152 of slide supply device 165 includes three cassette receivers 164 into which a cassette 10 loaded with slides 28 can be inserted. Right and left side walls 12 and 14 of cassette 10' each have two notches 38 (as shown in FIG. 9) that enter cassette receivers 164 to stabilize cassettes 10. Contactor 151, located inside cassette receivers 164 contacts, and upwardly lifts shutter 158 of installed cassette 10.

Figure 11:
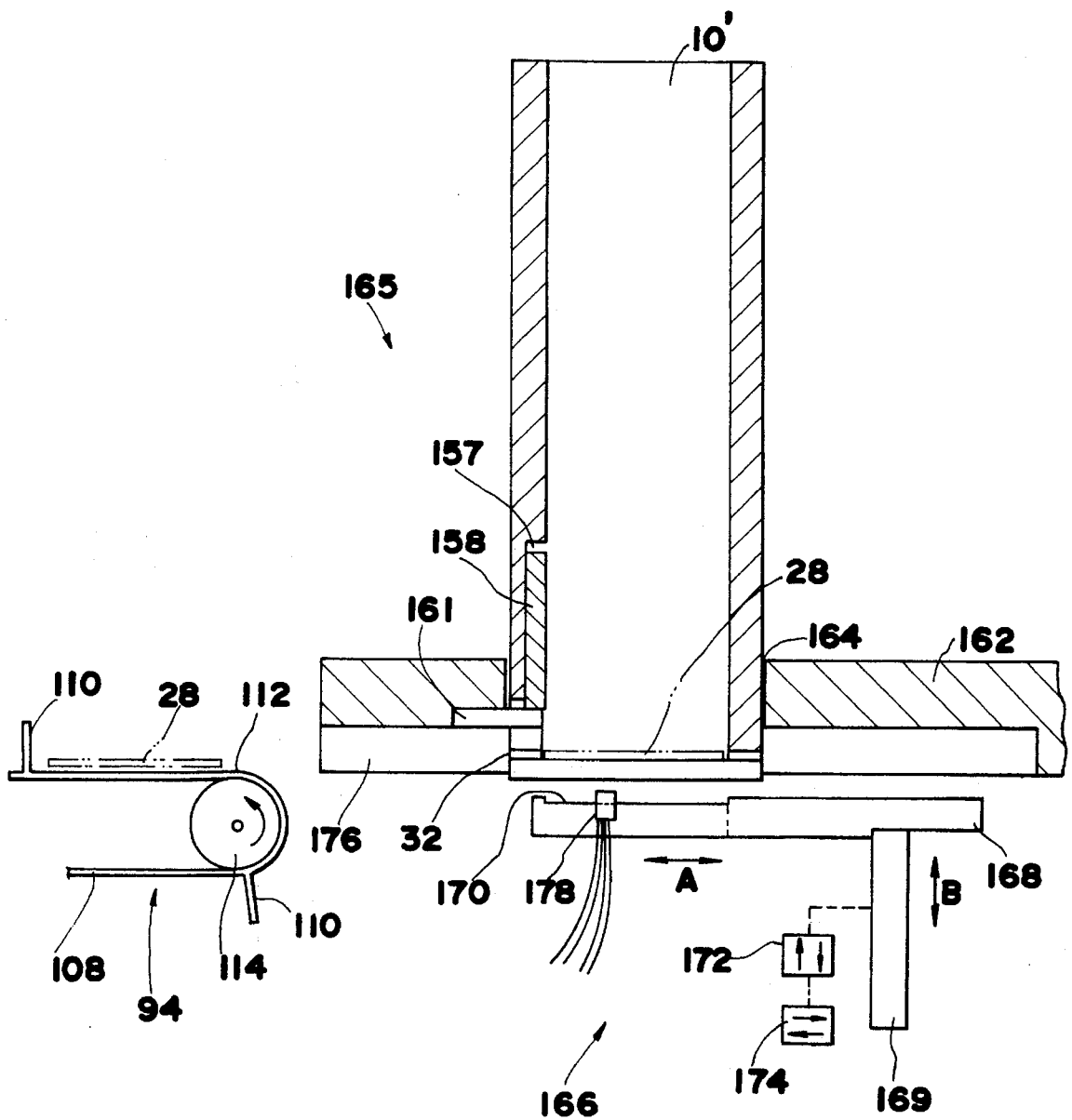
FIG. 11 is a cross section of the turntable supplying a blank slide to the conveyor.

Referring now to FIG. 11, there is shown a section view of turntable 162 with cassette 10 in place in cassette receiver 164. When cassette 10 is set in cassette receiver 164, contact of shutter 158 of cassette 10 with contactor 161 pushes shutter 158 upward, opening slide outlet port 32. Because cassette 10 has an outlet port 32 only on one side, contactor 161 makes it impossible for cassette 10 to be installed in cassette receiver 164 incorrectly.

A slide unloader 166 is located under turntable 162 to unload slides 28 from slide outlet port 32 of cassette 10, and send them to conveyor belt 108 of conveyor 104. To accomplish this, slide unloader 156 comprises a slide receiver 168 which is mounted on a support 169. A depression 170 in slide receiver 168 has a depth that is slightly less than the thickness of a slide 28. A conventional up/down drive 172, and a conventional face/aft drive 174 are connected to support 169 to lift slide receiver 168 up to engage bottommost side 28 and to move slide unloader 156 along a path 176 to place slide 28 on conveyor belt 108. Conveyor belt 108 is stepped one space 112 following the unloading of slide 28 from cassette 10 to present an empty space 112 to next slide 28.

A sensor 178 is disposed at a side of slide receiver 168 to determine the presence of a loaded cassette 10.

Figure 12:
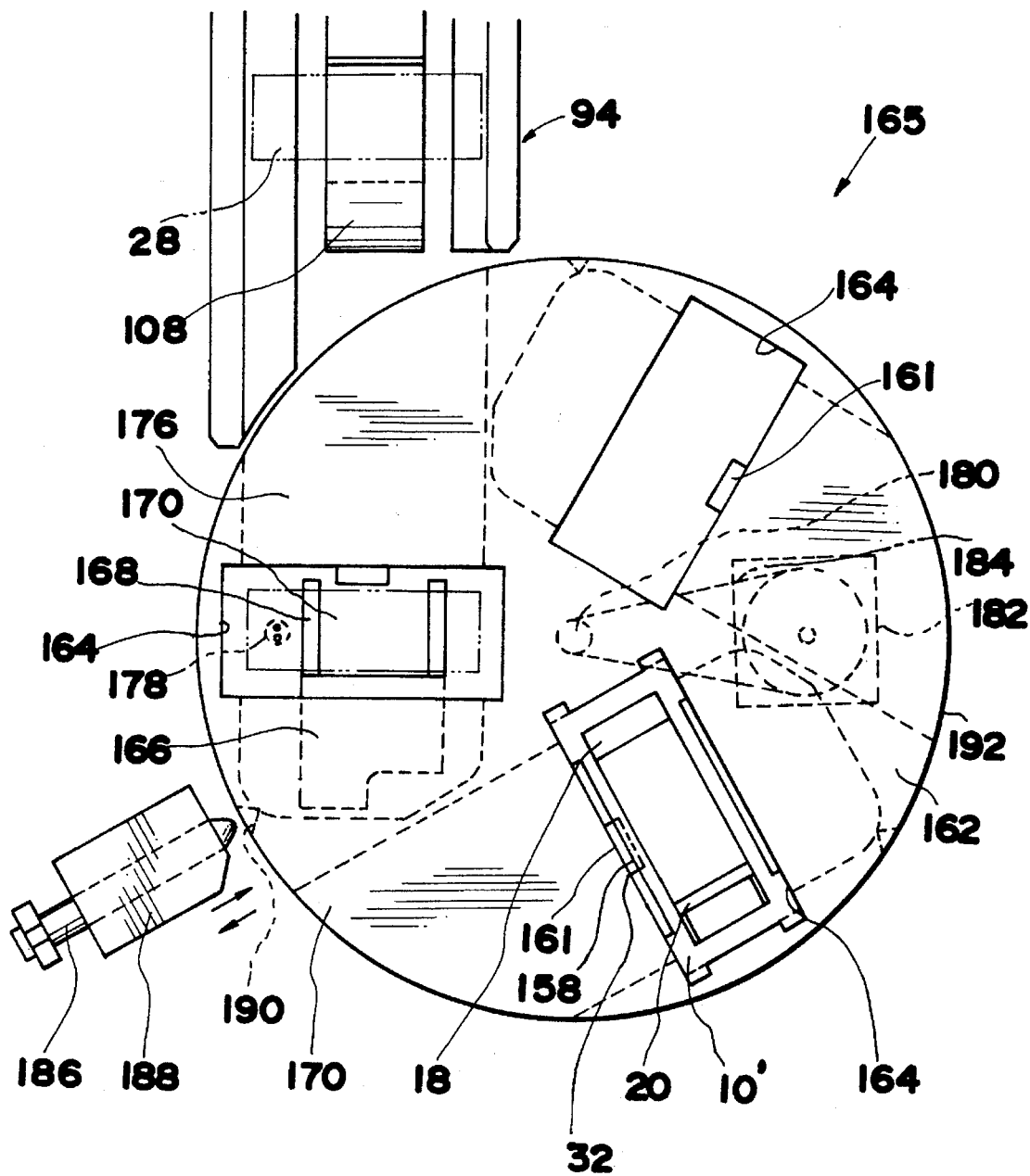
FIG. 12 is a plan view of an embodiment of the turntable slide supplying device according to the invention.

Referring to FIG. 12, cassettes 10', which hold, for example, 100 slides 28 each, are set in cassette receivers 164 in turntable 162. Turntable 162 is rotatably mounted on a shaft 180. Shaft 180 is turned and stopped by a controller/driver 182 driving a belt 184. The stop position is determined by sensor 178, which is oriented in an upward looking direction from under turntable 162, centered on the outer edge of depression 170 of slide receiver 168. When a cassette receiver 164 with a cassette 10' loaded with slides 28 is installed over slide receiver 168, a signal from sensor 178 causes a controller/driver 182 to stop turntable 162 and to engage a bolt 186 of a lock 188 in a notch 190, thereby locking turntable 162 in place. Three notches 190 are disposed around an edge 192 of turntable 160. Each notch 190 corresponds to one of the three positions in which a cassette receiver 164 can be positioned.

Any other suitable locking devices may be substituted for lock 188 and notches can be substituted, without departing from the spirit of the invention. For example, a lock 188' can utilize a bolt 186' which moves upward to engage and lock turntable 162 as shown in FIG. 10.

Referring now to FIGS. 11 and 12, sensor 178, which may be any suitable device such as, for example, a photo detector. In a convenient embodiment, sensor 178 includes a light source, projected upward, and a photodetector integrally formed therein. Sensor 178 continually checks for the presence of a slide 28 in cassette 10' by sensing reflection of its light source from frosted area 96 of slide 28. When the presence of a stack of slides is sensed, the slides 28 are unloaded one by one by slide unloader 166.

When cassette 10 is empty, sensor 178 causes turntable 162 to rotate 120 degrees, thereby positioning the next cassette 10' for unloading as described above.

Because turntable 162 can hold three or more cassettes 10', there is no need to stop the device when a cassette 10' is empty. The empty cassette 10' can be reloaded or replaced by a loaded cassette 10' before the remaining two cassettes 10' are emptied.

Slides 28 move along path 176 under turntable 162 and slide receiver 168 to reach conveyor belt 108 properly oriented for subsequent operations.

Figure 13:
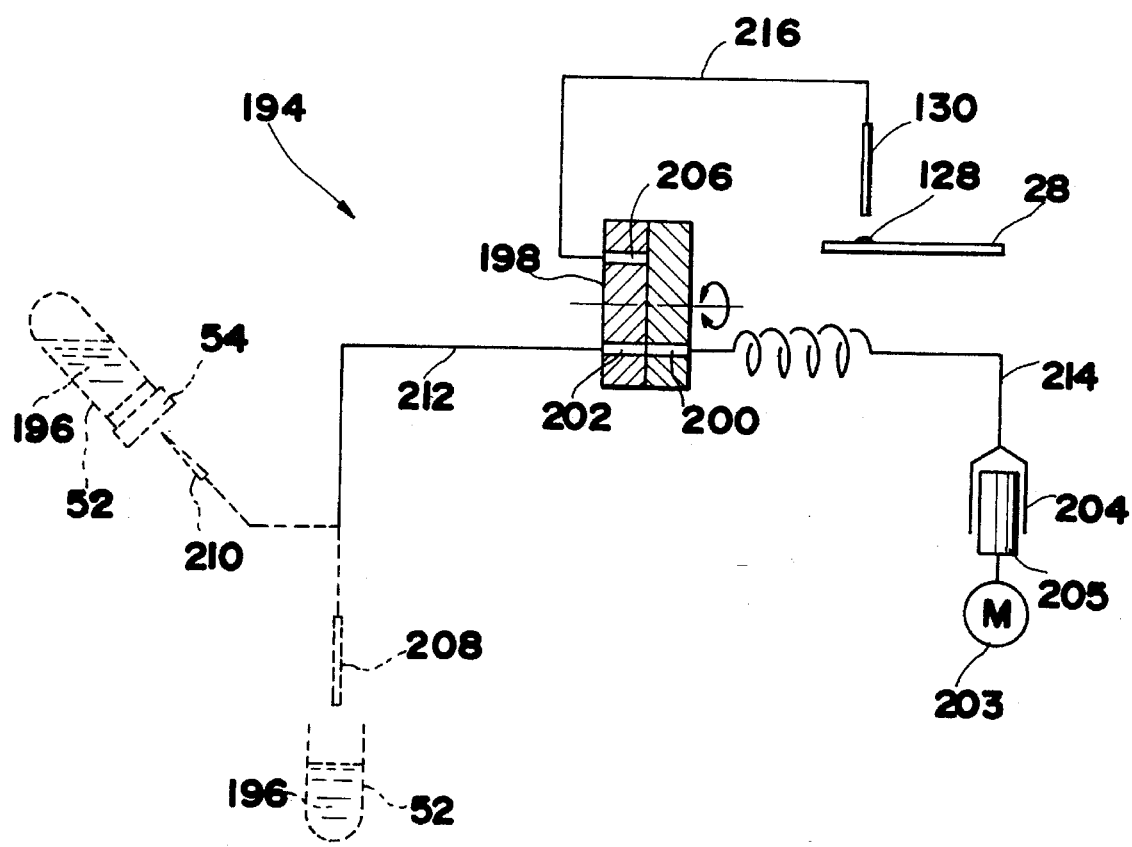
FIG. 13 is a flow diagram of a hydraulic circuit to drop a blood sample on a slide.

Referring to FIG. 13, there is shown a hydraulic circuit 194 for dispensing a blood sample 196 from sample containers 52 to slides 28 for smearing. A two position valve 198 controls the flow of blood from sample container 52 to slide 28.

A syringe operator 203 drives a piston 205 in a syringe 204 to draw and force a sample blood through hydraulic circuit 194.

In a first position of valve 198, a port 200 is open to an inlet port 202, forming a complete path for blood to be drawn from sample container 52 to syringe 204. In a second position of valve 198, port 200 is open to outlet port 206, thereby forming a complete path for blood between syringe 204 and dropper 130 to place blood drop 128 on slide 28. With valve 198 in the first position, syringe 204 draws blood sample 196 under control of syringe operator 203 from an open sample container 52 through a thin pipette 208, or from a sample container 52' with a rubber stopper 54 through a hypodermic needle 210, an inlet tube 212, inlet port 202, port 200 of valve 198, and a syringe tube 214 to syringe 204.

When syringe 204 is filled with blood, valve 198 is switched to its second position. Blood is forced by syringe 204 through syringe tube 214, port 200 and outlet port 206 of valve 198, and dropper tube 216 to dropper 130 from which it is dropped on slide 28. In this way, blood sample 196 is dispensed at a location that is relatively distant from that at which it was drawn without moving connecting tubes.

Figure 14:
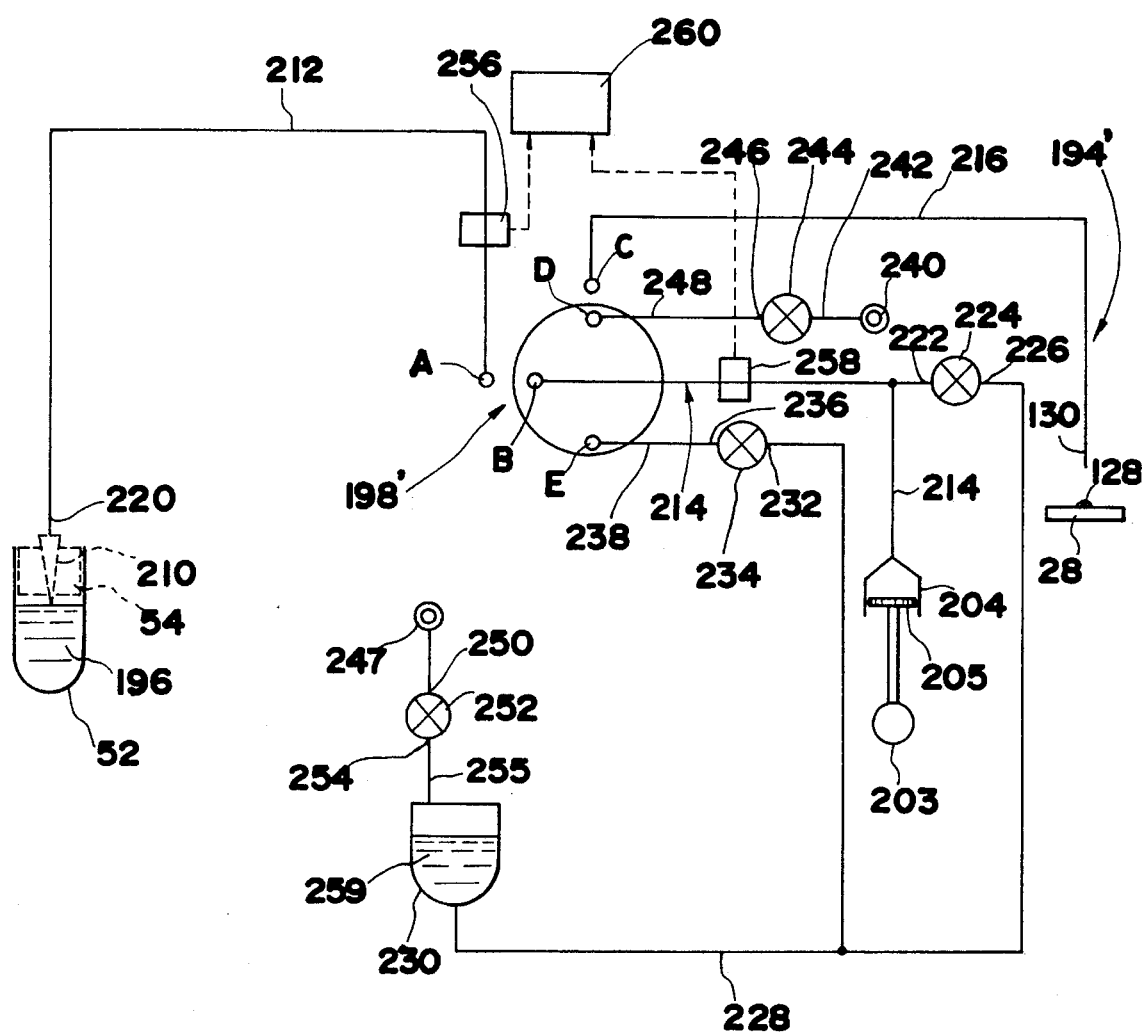
FIG. 14 is a flow diagram of another embodiment of a hydraulic circuit to drop a blood sample on a slide with blood viscosity detection and washout capability.

Referring to FIG. 14, there is shown a schematic diagram of a second embodiment of a hydraulic circuit 194' for dispensing blood sample 196 from sample containers 52 to slides 28 for smearing.

A switching valve 198' having ports A, B, C, D, and E includes first and second conditions. In the first condition (as shown in FIG. 14), a port A is connected to a port B, and a port C is connected to a port D. In the second position, port A is connected to a port E, and port B is connected to port C.

A first end of inlet tube 212 is connected to port A of valve 198'. A second end 220 of inlet tube 212 is in position to draw blood from sample container 52. Inlet tube 212 may be a simple tube or it may have a needle 2 10 (shown in phantom) at end 220. The presence or absence of needle 210 depends on whether or not sample container 52 is sealed by a rubber stopper 54 also shown in phantom. Port B of valve 198' is connected to a first end of tube 214. A second end of tube 214 is connected to a syringe 204, thereby communicating port B to syringe 204. A third end of tube 214 is connected to an outlet port 222 of a washer valve 224. An inlet port 226 of washer valve 224 is connected by one leg of a Y-shaped tube 228 to a washer 230. A second leg of Y-shaped tube 228 connects washer 230 to an inlet port 232 of washer valve 234. An outlet port 236 of washer valve 234 is connected to port E of valve 198' by a tube 238.

Port C is connected to a first end of dropper tube 216. A second end of dropper tube 216 is connected to dropper 130. Dropper 130 is positioned over slide 28 to deposit a blood sample 196 for smearing. A positive pressure source 240 is connected through an inlet port 242 of an air valve 244, outlet port 246, and a tube 248 to port D of valve 198'. A second positive pressure source 247 is connected through inlet port 250 of an air valve 252, an outlet port 254, and an air tube 255 to washer 230.

Sample sensors 256 and 258 are positioned on inlet tube 212 and syringe tube 214, respectively, to send blood detection signals to a timer 260. Timer 260 determines the thickness of blood sample 196 by measuring the time required for blood sample 196 to move between sample sensors 256 and 258.

With valve 198' in the first position shown in FIG. 14, and syringe 204 in the drawing mode, syringe operator 203 pulls a piston 205 in an outward direction, causing blood sample 196 to be drawn, thus filling inlet tube 212, valve 198', and a part of syringe tube 214 up to sensor 258.

Next, switching valve 198' switches to its second position and syringe 204 is activated in the discharge mode. The blood sample 196 is fed through valve 198' ports B and C, dropper tube 216, and dropper 130 onto slide 28. As soon as delivery of blood drop 128 is completed, valves 252 and 234 are opened to permit driving of washer fluid 259 from washer 230 by pressure in positive pressure source 240 through tube 249, inlet port 250 of air valve 252, and air tube 255 to clean the inside of tube 212, end 220 and needle 210, if used.

Switching valve 198' returns to its initial position. Syringe 204 is returned to the drawing mode to draw in additional washer fluid 259. Switching valve 198' switches to its alternate position, and valve 226 is closed. Syringe 205 is switched to the discharge mode to drive washer fluid 259 through dropper tube 216 and dropper 130, thereby cleaning these parts.

Switching valve 198' then returns to the initial condition, valve 252 is open to pass air from positive pressure source 240, emptying tube 216.

First sensor 256 is located near switching valve 198' on inlet tube 212. Second sensor 258 is located near switching valve 198' on syringe tube 214. First and second sensors 256 and 258 are identical, thus only first sensor 256 is described in detail.

Figure 15:
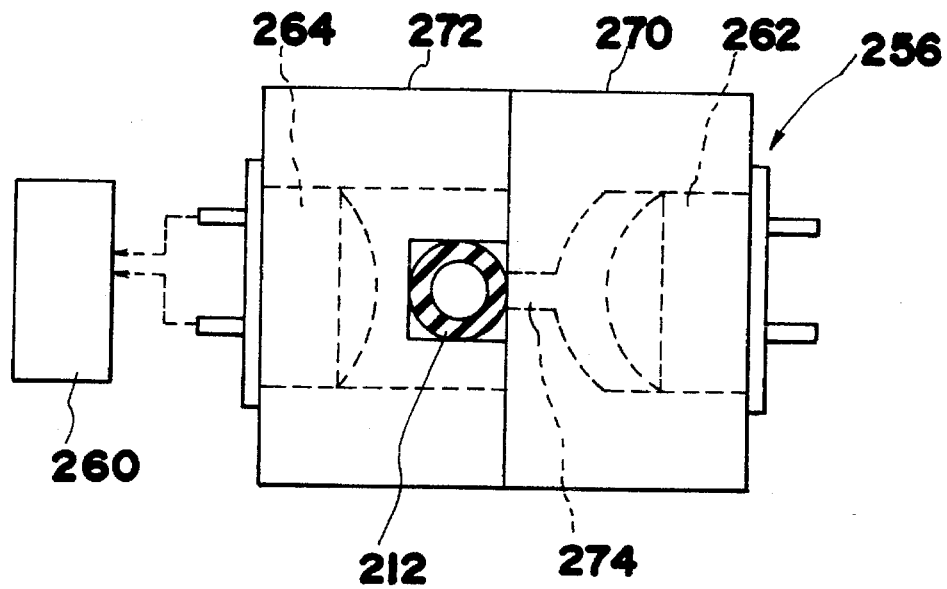
FIG. 15 is a detailed view of the blood flow detection sensors shown in FIG. 16.

Referring now to FIG. 15, sensor 256, viewed from the direction perpendicular to tube 212, comprises a light emitter 262 such as an LED, a light receiver 264 such as a phototransistor, and supports 270 and 272. Supports 270 and 272 support inlet tube 212. The light from light emitter 262 illuminates inlet tube 212 through a slit 274. Inlet tube 212 (as well as syringe tube 214) is made of light transmitting material such as, for example, glass or transparent synthetic resin.

When a blood sample is present in tube 212, an electric signal output by light receiver 256 is sent to a timer 260. Before drawing blood sample, tube 212 at sensor 256 contains air or washer fluid 259. Therefore, tube 212 transmits light. When tube 212 is filled with blood sample 196, the light to light receiver 264 is at least partially blocked. The resulting signal to timer 260 indicates the presence of blood. The time duration from the initiation of drawing to the detection of blood by sensor 256 can be used for determine the thickness or viscosity of blood sample 196. Thick blood flows more slowly than thin blood under the same conditions of syringe 204.

Returning now to FIG. 14 the illustrated embodiment of hydraulic circuit 194 provides a fixed path length over which the movement of the leading edge of blood sample 196 can be timed. That is, the flow distance between sensors 256 and 258 is fixed, and is independent of external tube lengths such as inlet tube 212. Thus, a measurement of the time required for the leading edge of blood sample 196 to pass from sensor 256 to sensor 258 can be interpreted in terms of the thickness of the blood sample 196. As a consequence, the thickness measurement is accurate.

Figure 16:
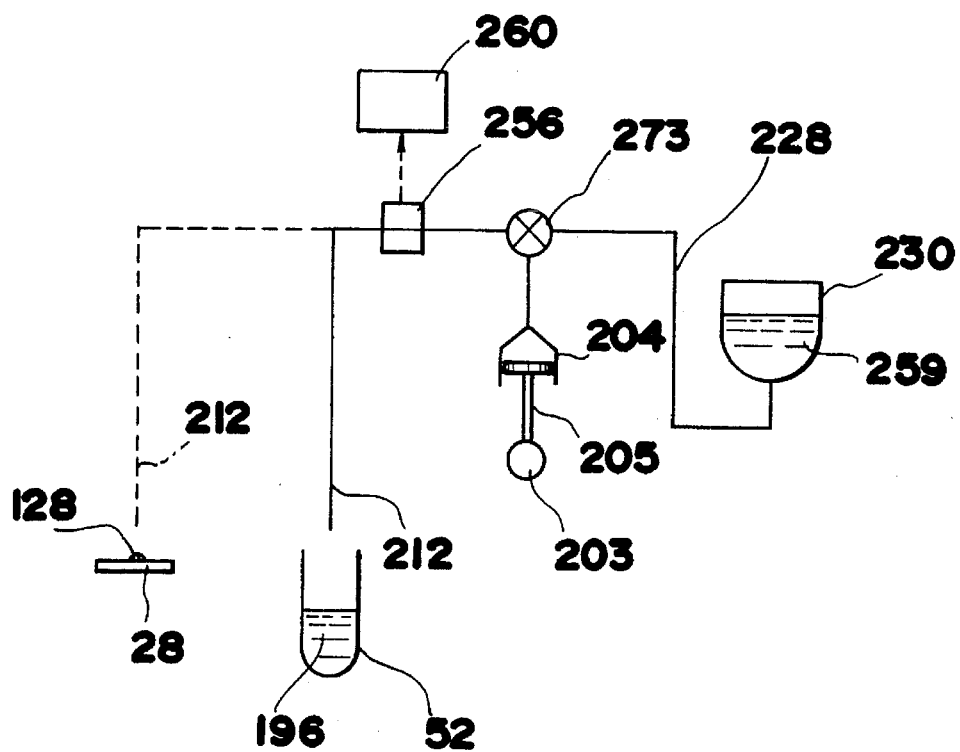
FIG. 16 is another embodiment of a hydraulic circuit to drop a blood sample on a slide using viscosity detection and washout capability.

Referring to FIG. 16, another embodiment of a hydraulic circuit 194 employs inlet tube 21.2 connected to syringe 204 through a two way valve 273. Initially, two way valve 273 is in a position connecting inlet tube 212 to syringe 204. Sample container 52, containing blood sample 196 is placed under the end of inlet tube 212. Blood sample 196 is drawn through inlet tube 212 as far as sensor 256 by syringe 204.

The time from the initiation of drawing to the sensing of blood sample 196 by sensor 256 is measured by timer 260. Inlet tube 212 is moved to a position over slide 28 and the action of syringe 204 is reversed, dropping blood sample 196 onto slide 28 to form blood drop 128 thereon. Two way valve 273 is changed to a position connecting syringe 204 to tube 228. Syringe 204 is operated to draw in a quantity of washer fluid 259 from washer 230. Two way valve 273 is changed to its original position connecting syringe 204 to inlet tube 212. Washer fluid 259 is expelled from syringe 204 to clean sensor 256 and inlet tube 212. The process can then be repeated with another blood sample 196.

Figure 17:
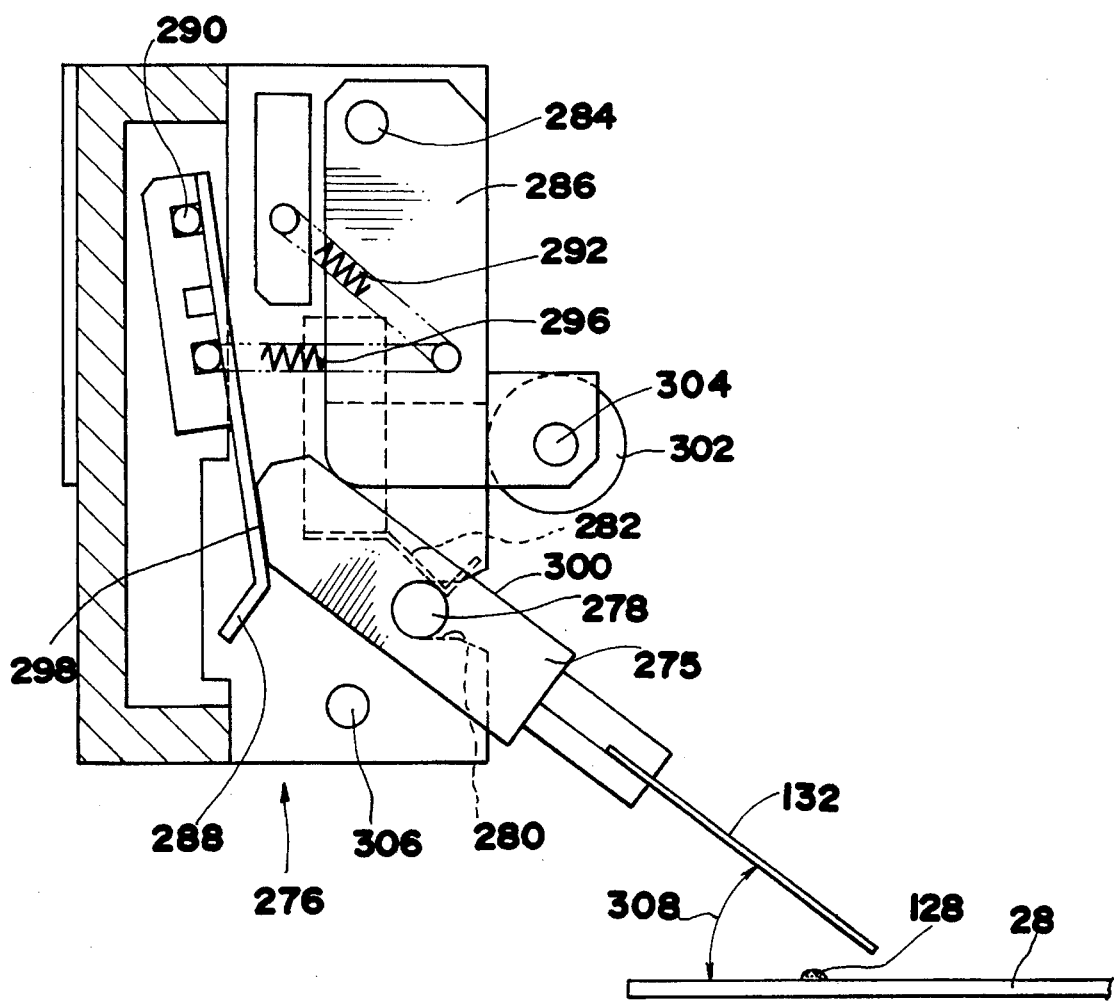
FIG. 17 is a cross-sectional view, taken in the direction A in FIG. 7, of an automatically adjustable blood smearing device shown in the smearing position.

Referring to FIG. 17, a smearing glass 132 is held by a glass holder 275, which is pivotally secured to a smearing fixture 276 by a shaft 278. Shaft 278 is rotatably and removably secured in a notch 280 by the pressing action of a flat spring 282. Glass holder 275, together with shaft 278 can be removed by pulling strongly to the fight, as shown in FIG. 17. At an upper portion of smearing fixture 276, a shaft 284 pivotally supports an arm 286. A flat spring 288 is pivotally supported by a shaft 290. A first side of a coil spring 292 is connected to smearing fixture 276. A second side of coil spring 292 is connected to arm 286. The spring action of coil spring 292 tends to hold arm 286 against smearing fixture 276. A first side of a coil spring 296 is connected to arm 286. A second side of coil spring 296 is connected to flat spring 288. This pulls flat spring 288 against a heel 298 of glass holder 275, while arm 286 is pressed against an upper surface 300 of glass holder 275. A beating 302 is rotatably attached to arm 286 by a shaft 304.

The mounting of smearing fixture 276 (not shown) allows it to be moved both horizontally and vertically in its position in smear generator 60, shown in FIG. 7. This movement can be accomplished by a number of available conventional means, for example, a timing belt to which holder 274 is attached and which is hung between two pulleys, one of which is driven by a stepping motor while the other is fixed to smear generator 60.

Because glass holder 275 is held firmly in position between arm 286 and flat spring 288 by coil springs 292 and 296, when smearing fixture 276 moves downwards, smearing glass 132 is pressed firmly against slide 28. An angle 308 between smearing glass 132 and slide 28 can be varied to achieve the desired smear thickness by adjusting the downward travel of smearing fixture 276. A largest angle 308 between smearing glass 132 and slide 28 occurs when smearing glass 132 lightly touches slide 28. Continuing descent of smearing fixture 276 causes glass holder 275 to pivot counterclockwise on shaft 278 against the pressure of flat spring 288 and coil springs 292 and 296, so that as smearing fixture 276 is lowered, angle 308 becomes more acute while good contact between smearing glass 132 and slide 28 is maintained.

Once angle 308 is adjusted to the correct value for the measured thickness of the blood sample being prepared, smearing glass 132 is pulled along slide 28 with good contact as smearing fixture 276 moves horizontally in a direction parallel to the surface of slide 28 to smear blood sample 196 on slide 28. Varying the speed with which smearing glass 132 is drawn across slide 28 also controls the thickness of the smear.

After the blood smear is made, smearing glass 132 is washed in glass washer 136 (see FIG. 7).

Figure 18:
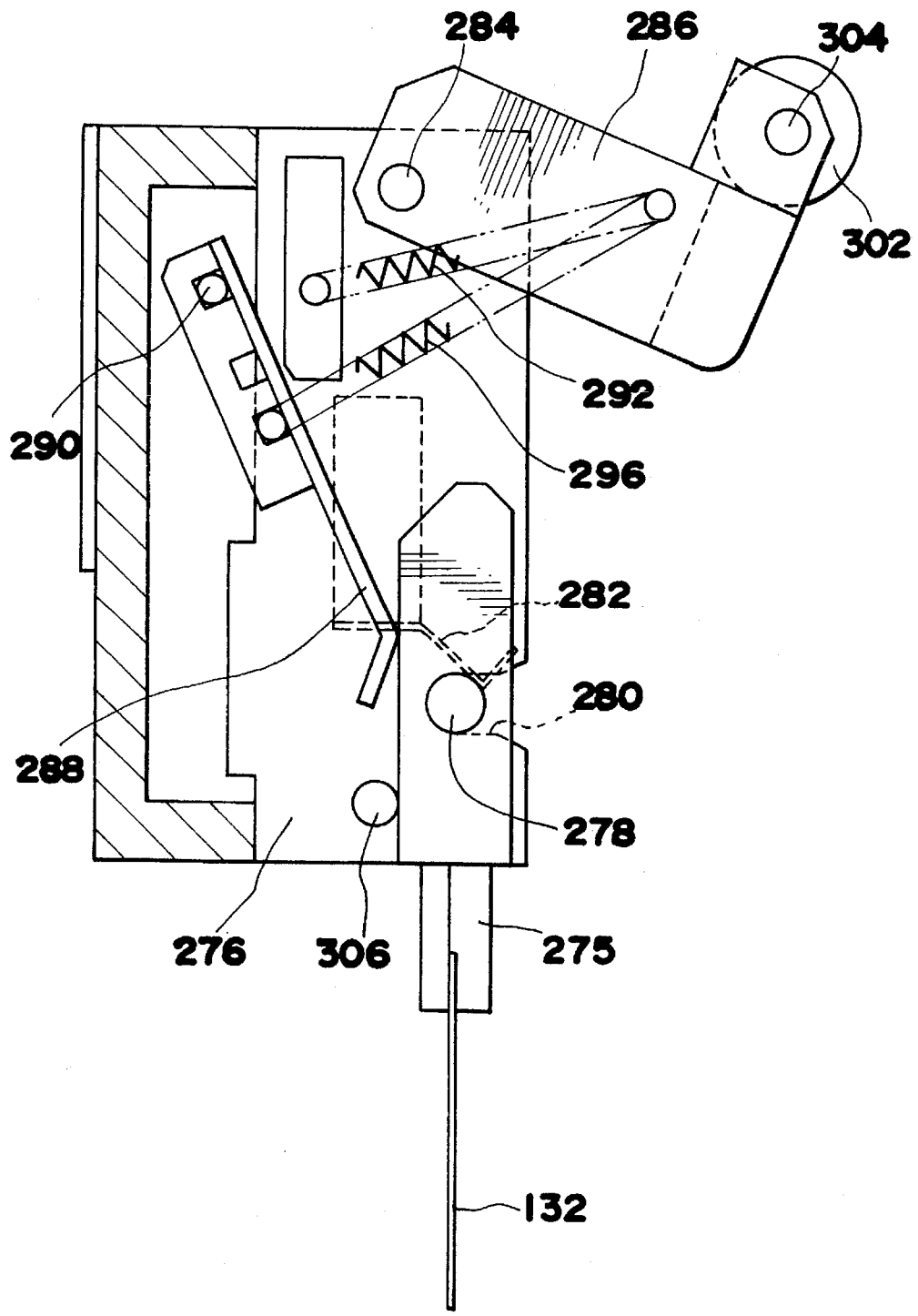
FIG. 18 is a cross-sectional view, taken in the direct A in FIG. 7, of an automatically adjustable blood smearing device shown in the washing position.

Referring now to FIG. 18 a vertical cross section of smearing fixture 276 shows glass holder 275 in position for washing smearing glass 132.

After a smear is made, and slide 28 is moved out of the way, smearing fixture 276 is lowered further until a lever or the like (not shown) blocks downward motion of bearing 302 on arm 286. Further downward motion of smearing fixture 276 forces arm 286 to pivot upward about shaft 284, pulling flat spring 288 forward with coil spring 296 and rotating glass holder 274 and smearing glass 132 to the vertical position against a stop 306. This places smearing glass 132 in vertical position appropriate to enter and be washed in washer 136 (FIG. 7) as smearing fixture 276 continues to descend.

Figure 19:
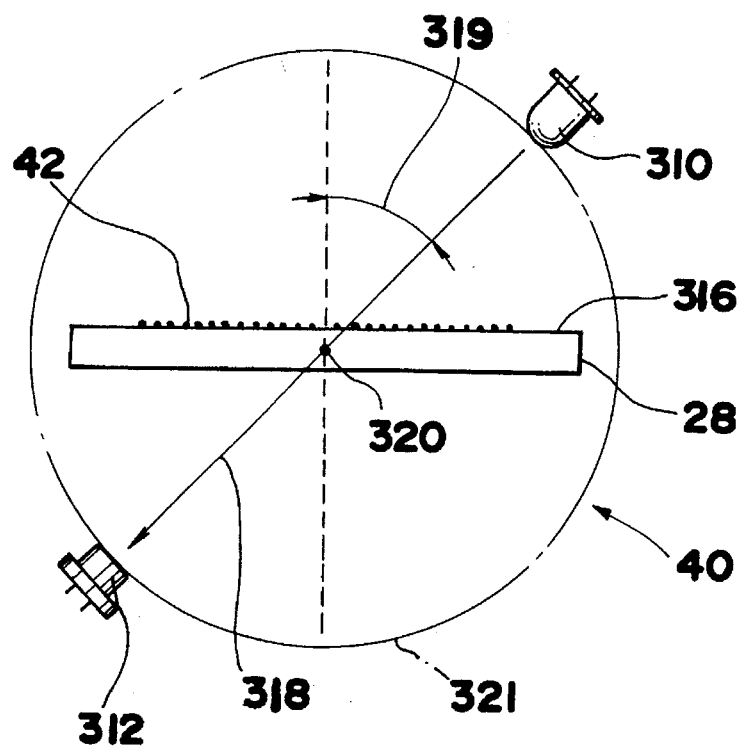
FIG. 19 is a perspective view of an embodiment of the diagonally positioned smear detector according to the invention.

Referring to FIG. 19, a light emitter 310, which may be, for example, an infra red emitting LED, and a light receiver 312, such as a photo diode, are disposed on opposite sides of a slide 28 having a smear 42 on its surface 316. A light beam 318 from light emitter 310 passes through smear 42 and slide 28 at an axis 320 to light receiver 312. When the surface of slide 28 is clean, substantially all of the light emitted by light emitter 310 reaches light receiver 312, indicating that no smear 42 is present. An alarm output is generated by light receiver 342. When a smear 42 is present the light received by light receiver 312 is reduced, indicating that a smear 42 has been made and no alarm signal is generated.

Figure 20:
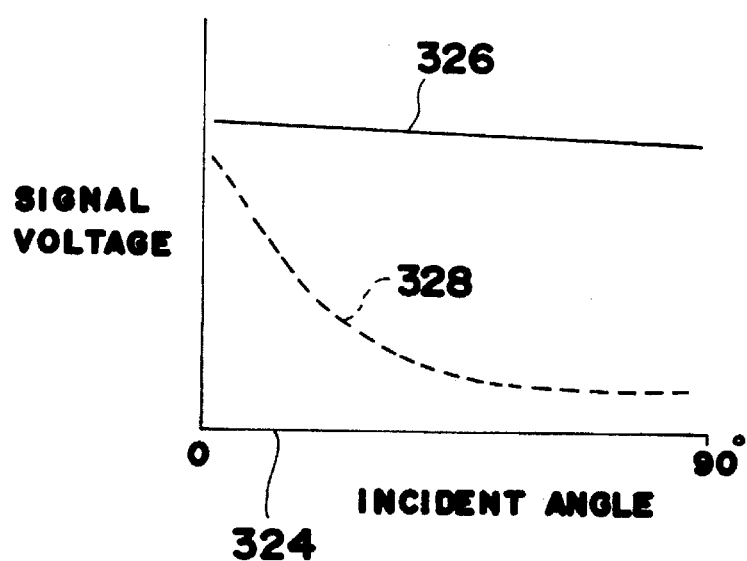
FIG. 20 is a graph representing the relationship between an incidence angle and the signal-to-voltage level detected by the diagonally positioned smear detector.

FIG. 20 shows a graph 324 that represents a relationship between incidence angle 318 and a signal voltage level output from light receiver 312. The signal level is measured by the output voltage of light receiver 312 as it moves around axis 320 of slide 28, while maintaining its relationship to light emitter 310. In FIG. 19, a broken line 321 depicts a circle centered at axis 320. Both light emitter 310 and light receiver 312 are placed on circle 321. Infrared light from light emitting device 310 passes through slide 28 at center axis 320 to reach light receiver 312.

Referring again to FIG. 20, a solid line 326 shows voltage changes in the output of light-receiving device 312 with no blood smear 42 on slide 28. A dotted line 328 represents the voltage changes with a smear 42 on slide 28. Without smear 42, the output voltage declines as the incidence angle 319 increases. That is, the larger incidence angle 319 gets, the larger the difference between a signal made with smear 42 and a signal made without smear 42.

The reason for this is that the amount of light interrupted by particles such as blood cells increases as incidence angle 319 increases.

To achieve the desired result, incidence angle 319 must be greater than 0 degree and less than 90 degrees. For practical reasons, an angle 319 of between 30 degrees and 75 degrees is the preferred embodiment and an angle 319 of between 50 degrees and 70 degrees is the most preferred embodiment.

Figure 21:
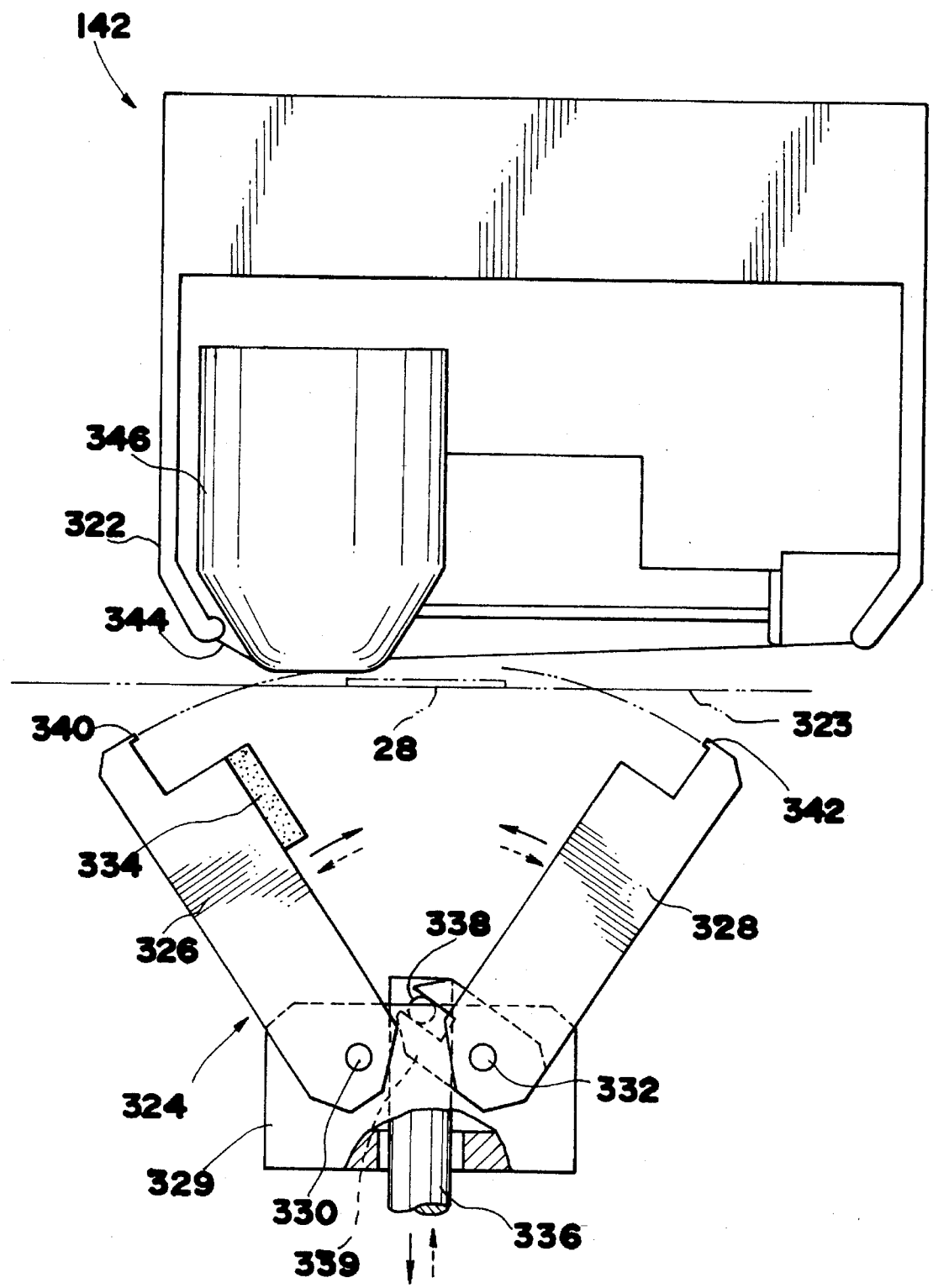
FIG. 21 is a perspective view of an embodiment of the smeared slide sample code printer.

Referring to FIG. 21, a printer head 322 of printer 142 is positioned directly above a slide 28 that is supported on a guide plate 323. Guide plate 323 steps slides 28 under the printer one at a time where identifying codes are printed on them.

A holder 324, which is positioned directly under the printer head 322 to hold slide 28 during printing, comprises a pair of arms, 326 and 328. Arms 326 and 328 are pivotally attached to a support 329 by pins 330 and 334, respectively. A piston 336, that is driven by a pneumatic source (not shown), extends vertically through support 329. Piston 336 is attached at its topmost end by a connecting pin 338 to a crank 339. Crank 339 is attached to a pivoted end of arm 328 and slidably contacts a lower vertical surface of arm 326. When piston 336 is moved in a direction away from printer head 322, arms 326 and 328 are moved toward each other by the action of crank 339 and connecting pin 338. A shock absorber 334, disposed along an inner surface of arm 326, absorbs shock and prevents protrusions 340 and 342, that extend inwardly from the tops of arms 326 and 328, respectively, from breaking slide 28 as they close. Shock absorber 334 may be of any convenient material including, for example, a rubber or a foam rubber pad.

During operation, when a slide 28 is in position for printing, piston 336 is moved in a direction to close arms 326 and 328 on each other, thus placing protrusions 340 and 342 over opposite edges of slide 28. In this position, protrusions 340 and 342 hold slide 28 securely against guide plate 323 while printer head 322 prints an identifying code on the slide.

A ribbon 344 of printer head 322 both deposits ink on slide 28 and absorbs some of the impact shock of a printer pin 346, thereby preventing slide 28 from being cracked.

The force of the impact of printer pin 346 is sufficient to crush some of the surface hills 348 of frosted area 96 of slide 28, thereby allowing ink to penetrate the frosting for improved adhesion.

Figure 22:
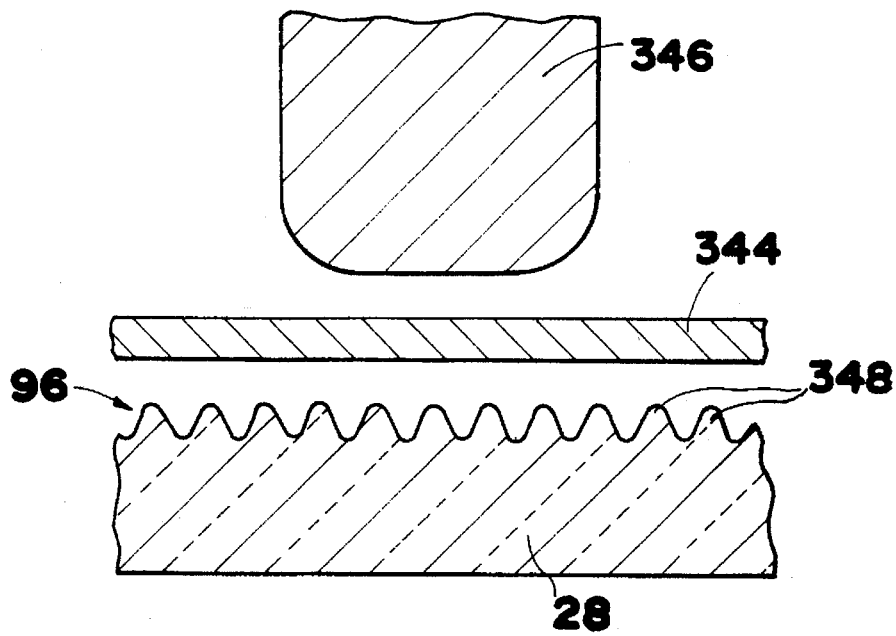
FIG. 22 is a schematic section view of the surface condition on the slide before impact of the printer pins.
Figure 23:
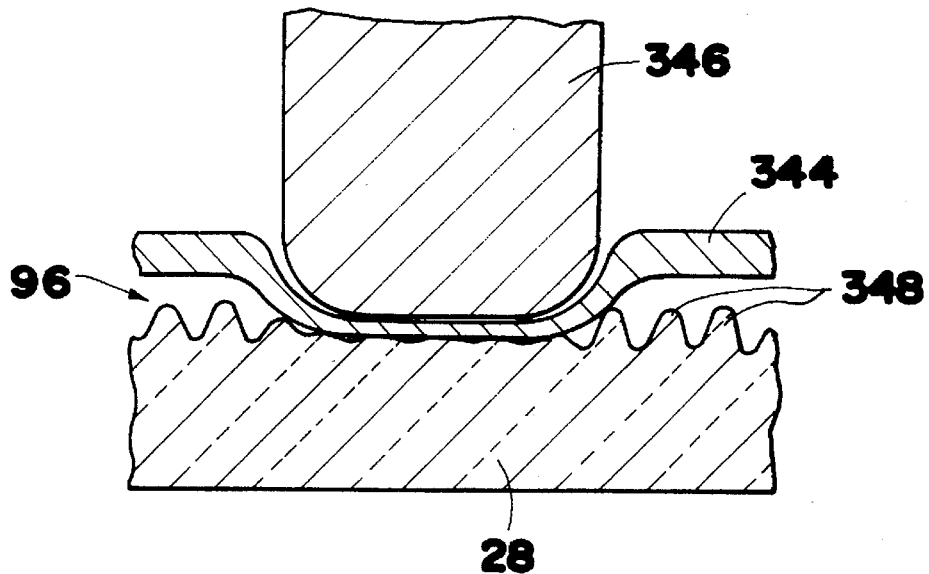
FIG. 23 is a schematic section view showing a printed condition on a slide.

FIGS. 22 and 23 illustrate the effect of the impact of printer pin 346 on frosted area 96. FIG. 22 is a greatly magnified representation of printer pin 346 poised above ribbon 344. Frosted area 96 of slide 28 shows a plurality of hill-like projections 348 greatly magnified.

Referring to FIG. 23, when printer pin 346 strikes ribbon 344, the force of the impact against frosted area 96 is sufficient to crush projections 348 driving ink down below the tops of surrounding projections 348, and applying a permanent identifying code that cannot be washed off slide 28.

Advantages of the described embodiment of printer head 322 include the use of an economical commercially available printer and the use of the impact of printer pin 346 to drive ink into fine concavities, providing ink with good adhesion.

Figure 24:
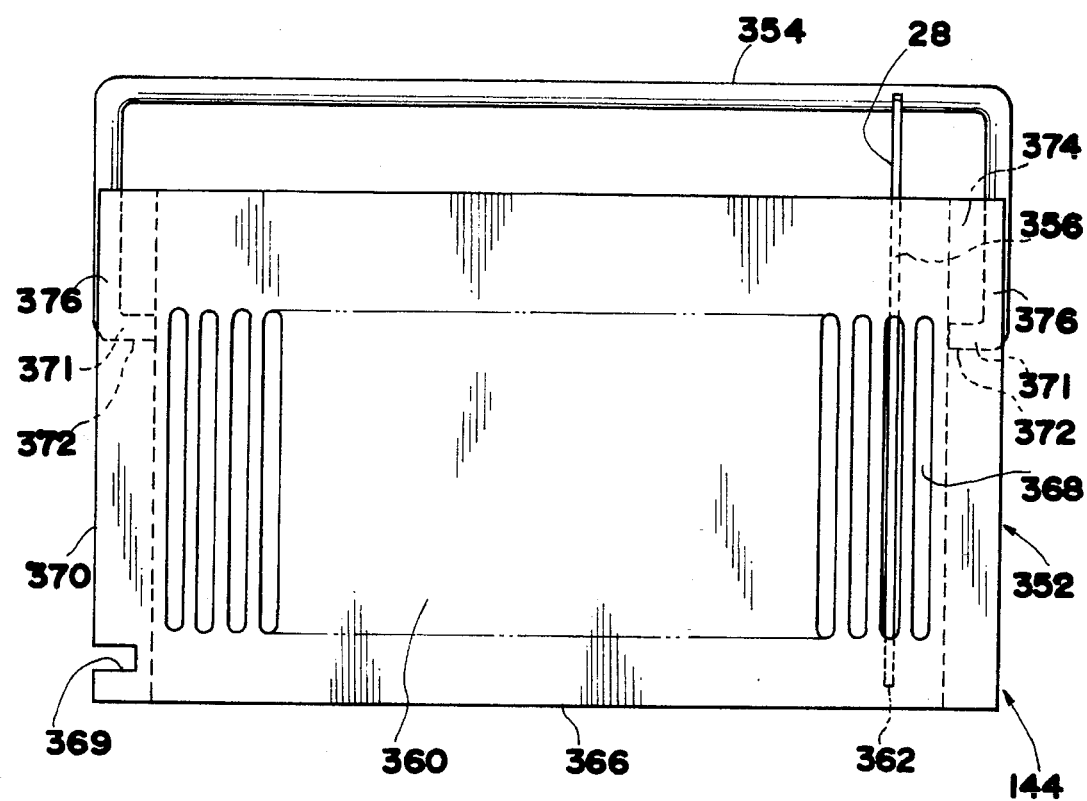
FIG. 24 is front view of an embodiment of a smeared sample rack according to the invention.
Figure 25:
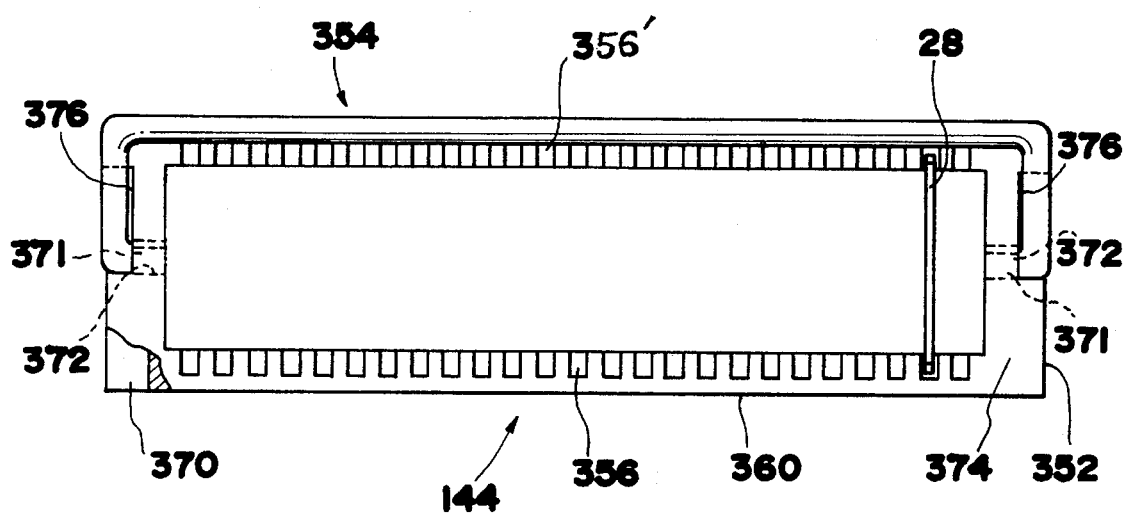
FIG. 25 is a plan view of the of the smeared sample rack.

Referring to FIGS. 24 and 25, smeared sample rack 144 comprises a cassette body 352 with a handle 354. Cassette body 352 is an open rectangle, having neither top or bottom walls. A plurality of vertical grooves 356, 356' are arranged in parallel on opposing inner facing surfaces of side walls 360. The widths of vertical grooves 356, 356' are slightly wider than the thickness of slide 28. Vertical grooves 356, 356' extend downward from the topmost edges of side walls 360 and end just above the bottom edges of side walls 360, forming a series of parallel slide storage positions 362. The bottom ends 364 of storage positions 362 prevent slides 28 from dropping through an open bottom 366 of cassette body 352. A V-shaped flare 357 at the top of grooves 356 facilitate entry of slides 28 into grooves 356.

Smeared sample rack 144 as illustrated, has positions for up to 25 slides 28. Slots 368 in both side walls 360 at each storage position allow air circulation through cassette body 352.

A guide notch 369, horizontally disposed across a lower portion of an end wall 370, engages a guide rail (not illustrated) of a transportation unit to be described.

Handle 354 is a thick wire that is bent to a U-shape. Ends 371 of handle 354 are bent inwardly and pivotally inserted into a handle slot 372 on each of end walls 370 and 374 for attachment to cassette body 352.

Figure 26:
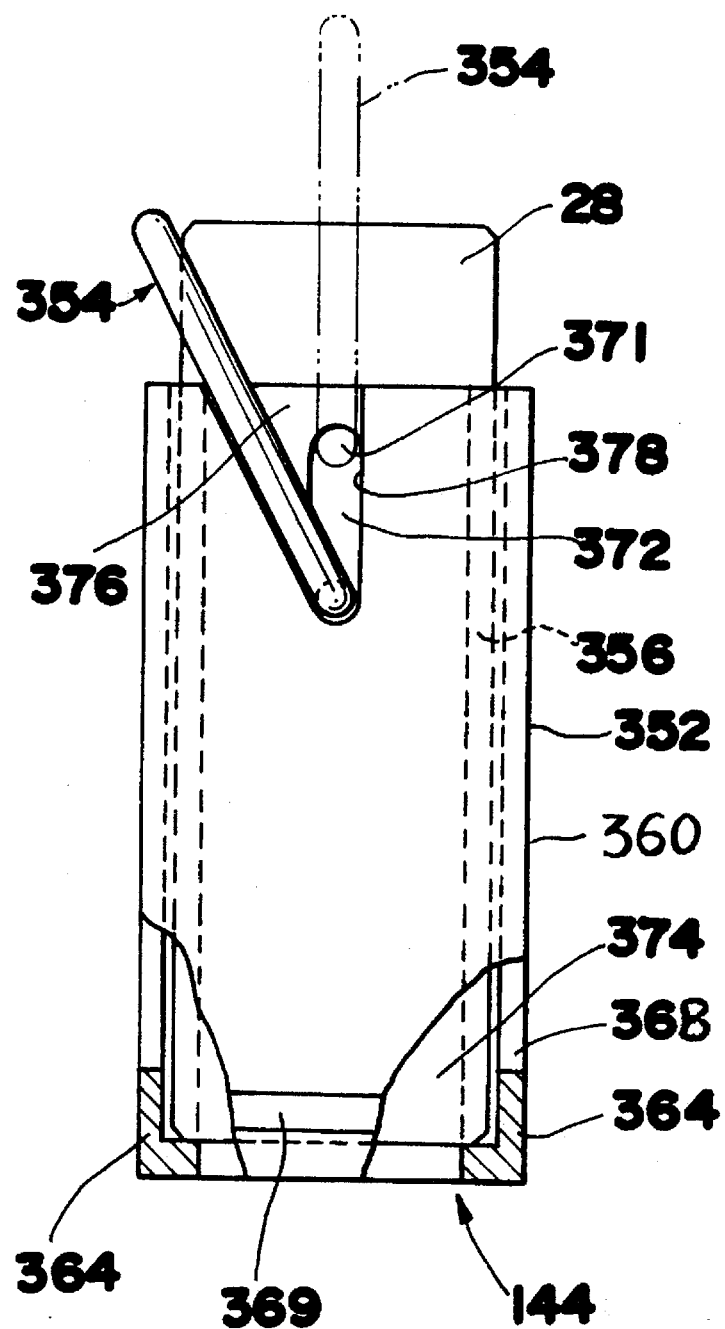
FIG. 26 is a side view of the smeared sample rack.

Referring to FIG. 26, it can be seen that an elongated shape of handle slots 372 allows handle 354 to be pulled up (indicated in phantom) for carrying or dipping smeared sample rack 144 into a smear staining bath (not shown).

V-shaped recesses 376 on the outer surfaces of end walls 374, that extend upward from the lowermost ends of handle slots 372, allow handle 354 to tilt to the left, as shown in the figure, when smeared sample rack 144 is positioned for receiving slides 28. V-shaped recess 376 allows handle 354 to tilt only in the direction shown, because of vertical edges 378 that block the movement of handle 354 beyond the vertical position in their direction. When handle 354 is released, it drops to the tilted position shown.

Because handle 354 can slope as shown, it is possible to attach two or more smeared sample racks 144 together at side walls 360 for shipping or collecting.

Figure 27:
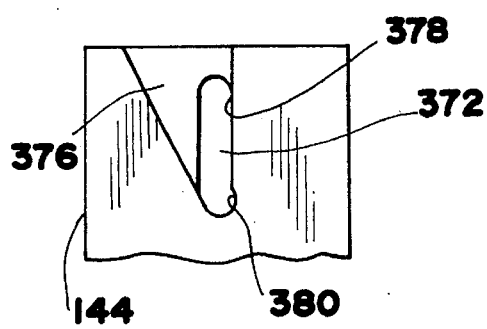
FIG. 27 is a left side view of the upper part of the smeared sample rack according to another embodiment of the invention.

Referring to FIG. 27, there is shown a second embodiment of smeared sample rack 144 from which handle 354 is omitted for purposes of explanation. Slot bottoms 380 of slots 372 are modified to extend under vertical edge 378. When handle 354 is released, ends 371 drop to slot bottoms 380, thus forcing handle 354 against vertical edge 378 and urging handle 354 to the desired position when it is released.

Figure 28:
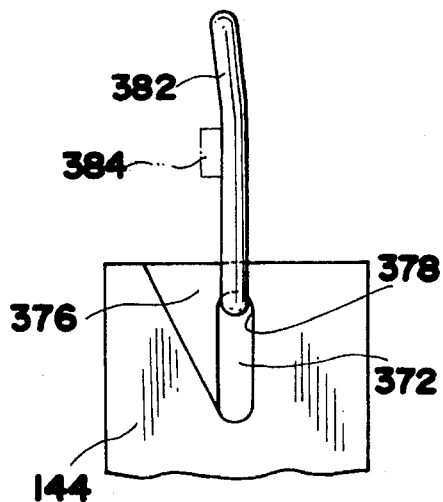
FIG. 28 is an upper left side view of the smeared sample rack according to another embodiment of the invention.

In still another embodiment of smeared sample rack 144, shown in FIG. 28, the shape of handle 354 is changed. In this embodiment, slots 372 are as described in FIG. 26, but handle 354 is unbalanced b) putting a bend 382 in it in the direction in which it is intended to tilt. A weight 384 can be added as shown in phantom to further unbalance handle 354.

Figure 29:
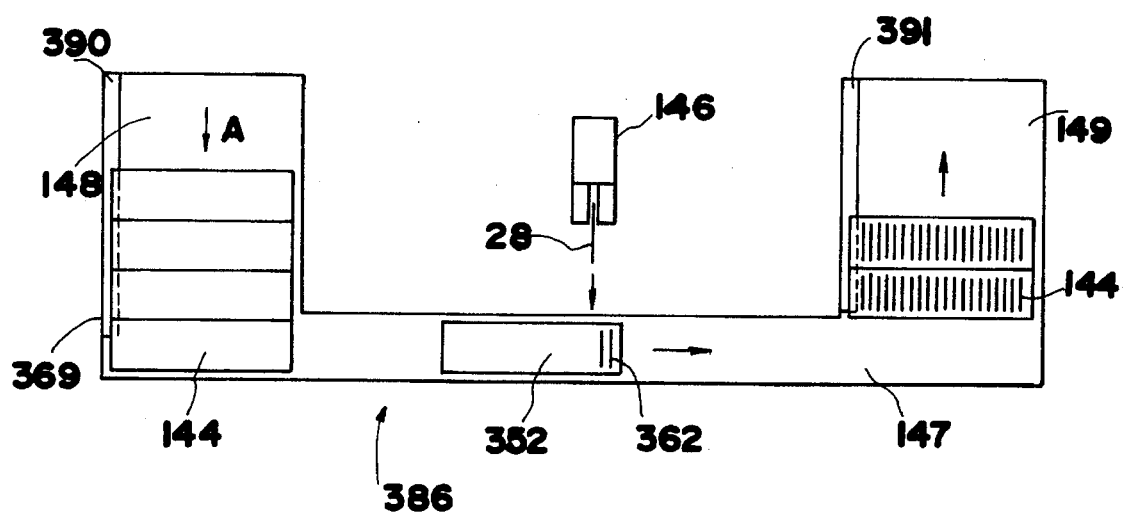
FIG. 29 is a plan view of a transportation unit of smeared sample racks in the smear generator.

Referring to FIG. 29, a U-shaped transportation unit 386 for smeared sample rack 144, has loading platform 148 with a cassette guide rail 390 parallel to its outer edge. Guide rail 390 engages notch 369 of empty smeared sample racks 144 (shown in FIG. 27). Guide rail 390 holds empty smeared sample racks 144 in proper alignment and prevents them from tipping over during transit to track 147 which is disposed at right angles to loading platform 148.

Smeared sample racks 144 are transported by track 147 to a position proximal to hand 146 for loading. They are then stepped along track 147, one storage position 362 at a time, as they are loaded with slides 28. When all storage positions 362 are filled, smeared sample rack 144 is transferred to unloader 149, located at an end of track 147, for removal from track 147. Guide rail 391 of unloader 149 engages notch 369 of smeared sample rack 144 to prevent it from tipping over.

A U-shaped path for smeared sample racks 144 is a simple arrangement making efficient use of space.

Blood analyzer system 49 of the invention is a complete apparatus for the analysis of blood and includes means for holding, transporting, handling and identifying blood samples, automatic blood analysis, and automatic blood smear generation.

Referring to FIG. 5, in operation, when sample racks 48 loaded with sample containers 52 individually labelled with a bar code identifier, are arranged in unloader 44, blood analyzer system 49 is started. The foremost sample rack 48 is transferred to conveyor 50 and is stepped in the direction indicated, passing through at least one of a blood analyzer 56, a reticulate blood corpuscle analyzer 58 and a blood smear generator 60 under the control of controller 62. Conveyor 50 steps one sample container position at a time and pauses at each position to allow blood analysis and sampling procedures to be completed.

Along conveyor 50, from right to left, there are a blood analyzers which may include a blood corpuscle analyzer 56 (e.g., Toa Medical Electronics NE-8000) and a reticulate red blood corpuscle analyzer 58 (e.g., Toa Medical Electronics R-1000), in addition to a smear generator 60. The NE-8000 is a blood corpuscle analyzer able to determine the five-classification data of white blood corpuscles in a blood sample, as well as to count blood components. The R-1000 is a reticulate red blood corpuscle analyzer with which a count of reticulate red blood corpuscles and their ratios in the blood sample are obtained.

Sample rack 48, conveyed by conveyor unit 14, stops at first blood analyzer 56 where a bar code identifier on the first sample container 52 is read by bar code reader 70. To assure that the bar code can be read, a rotator assembly 71 (shown in FIG. 6) slowly rotates sample container 52. First blood analyzer 56 records the bar code identifier and reports it and the results of its analysis of the blood sample contained in sample container 52 to system controller 62. A portion of the sample contained in sample container 52 is removed for analysis by first blood analyzer 56 using a needle and a hydraulic blood drawing circuit not shown. First blood analyzer 56 repeats this procedure for each sample container 52 stepped to it until all of the sample containers 52 in sample rack 48 have been analyzed. Sample rack 48 is then transported to second blood analyzer 58 which reads and records the bar code identifier of the sample containers 52 brought to it and reports the bar code and the results of each analysis to system controller 62 as did first blood analyzer 56.

Next, rack 26 is transported to smear generator 60. The bar code of each sample container 52 is read by bar code reader 70 of smear generator 70 and reported to controller 62. System controller 62 checks the reported bar code against the analyses reported for that bar code by blood analyzers 56 and 58. If the analyses indicate a normal blood sample, its sample container 52 is moved along and the next sample container stepped to smear generator 70. When system controller 62 identifies the bar code of an abnormal blood sample, smear code generator 70 is caused to make a smeared blood sample 138.

Sample racks 48 that have passed smear generator 70 on conveyor 50 are then transferred to unloader 44 for removal from blood analyzer system 49.

Figure 30:
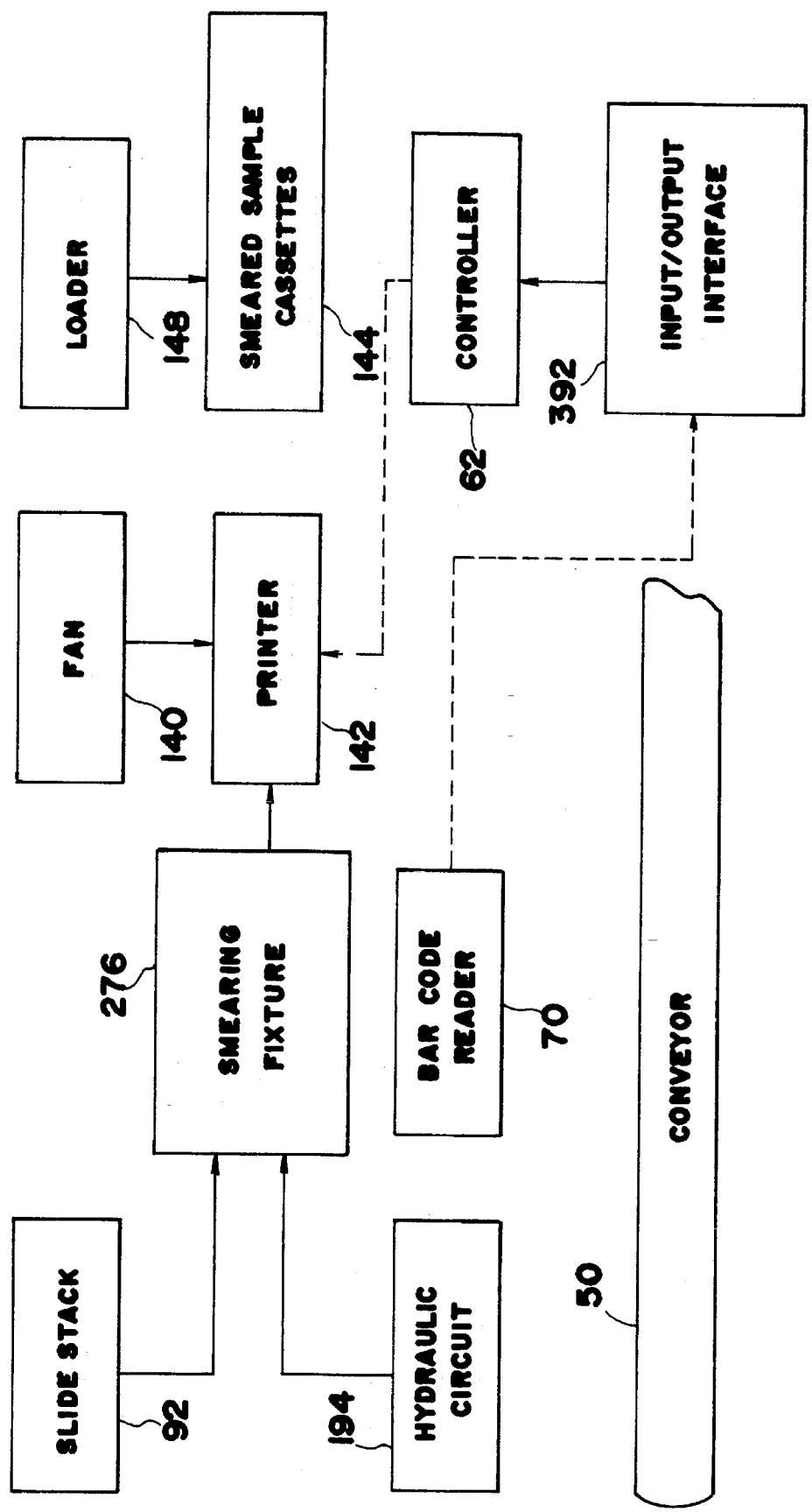
FIG. 30 is a functional block diagram of a smear generator according to an embodiment of the invention.

Referring to FIGS. 30 and 7, when the identifier of a sample container 52, read by bar code reader 70, is that of an abnormal blood sample, system controller 62 initiates the generation of a smeared blood sample 138. Conveyor 50 positions sample rack 48 with the subject sample container in position under hydraulic circuit 194, which draws blood sample 196 as shown in FIG. 13 from sample container 52 and drops a blood drop 128 on a slide 28. Blood drop 196 is then smeared by smearing glass 132 on slide 28 to form smeared blood sample 138. Smeared blood sample 138 is dried by fan 140. A smear detector 40 then checks that a smeared blood sample 138 has been properly prepared. When smear detector 40 detects a blank slide 28, an alarm is sounded, indicating a system failure.

The amount of blood sample 196 dispensed, file angle between smearing glass 132 and slide 28, and the smearing speed of smearing glass 132 are determined for each blood sample 196 by system controller 62 using data from blood analyzers 56 and 58. These smearing conditions are transmitted by system controller 62 to smeared sample generator 60 to control smearing glass 132.

The thickness of blood sample 196 may be determined by a blood analyzer 56 based, for example, on a percentage of hemoglobin present in blood sample 196, because the amount of hemoglobin correlates with thickness or viscosity. A high percentage of hemoglobin indicates a thick blood sample 196.

The time required by hydraulic circuit 194 to draw blood sample 196 from sample container 52 can also used to determine the thickness of blood sample 196. A thick blood 196 is drawn more slowly than a thinner blood.

System controller 62 controls the angle of smearing glass 132 against slide 28 and its smearing speed across slide 28 to prepare smeared blood samples 138 of the consistent thickness regardless of characteristics of blood sample 196 being smeared.

For thin blood, compared to a standard blood sample 196, system controller 62 commands at least one of the following adjustments:

(1) The amount of blood sample 196 to be smeared is increased, (2) The angle of smearing glass 132 is set larger, and (3) The pulling speed is increased.

For thick blood sample, compared to a standard blood sample 196, system controller 62 commands at least one of the following adjustments:

(1) The amount of blood sample 196 to be smeared is decreased, (2) The angle of smearing glass 132 is decreased, and (3) The pulling speed is reduced.

Slides 28 for supporting smeared blood samples 138 are taken from a slide storage source such as slide stack 92 and moved through the smear generation process by slide conveyor 94. Under the control of system controller 62, through an input output interface 392, printer 142 prints an identifying code on a frosted area 96 of slide 28c that corresponds to the bar code of sample container 52 from which blood sample 196 was taken.

A hand 146 then removes finished slide 28 from slide conveyor 94 and places it in smeared sample rack 144 for removal from the blood analyzer system 49.

As can be seen in FIG. 7, after each smeared blood sample 138 is made, smearing glass 132 is washed in glass washer 136, and dropper 130 is washed in dropper washer 134. In some embodiments of hydraulic circuit 194 a separate washing system is used, refer to FIGS. 14 and 15.

The present invention improves the efficiency of blood analysis compared with the prior art. Further, this system is flexible. If instructions are given to the system controller in advance, only selected samples are measured by the blood analyzers and smeared.

Improved efficiency also results from a smear generator 60 that is fully integrated into the remainder of blood analyzer system 49.

Flexibility is enhanced by the ability to program required analysis for each blood sample 196 into system controller 62.

Waste is eliminated because smeared blood sample. 138 are prepared only for abnormal blood as indicated by blood analyzer. 56 and/or 58.

Sample containers 52 can be capped with rubber stoppers without interfering with the blood sampling process, thus preventing the possible spread of blood infections.

The fully automatic operation of the blood analyzer system through smear generation saves labor cost.

Quality blood smears are assured because the correct blood smearing conditions are selected for each sample because the system utilizes a number of means for determining the thickness of individual samples.

Having described preferred embodiments of the invention with reference to the accompanying drawings, it is to be understood that the invention is not limited to those precise embodiments, and that various changes and modifications may be affected therein by one skilled in the art without departing from the scope or spirit of the invention as defined in the appended claims.

What is claimed is:

1. A slide supply device comprising:

a base;

means for accepting at least one cassette on said base;

said at least one cassette containing a plurality of slides;

said at least one cassette being removably aligned on said base by said means for accepting;

a slide outlet port in said at least one cassette;

said slide outlet port positioned to allow an individual slide of said plurality of slides to pass through transversely from said cassette;

dispersing means to sequentially disperse said plurality of slides;

closing means being vertically movable on said cassette with a first open position and a second closed position;

said first open position effective to enable said dispersing means;

said second closed position effective to prevent said plurality of slides from passing through said outlet port; and cooperating means, between said cassette and said means for accepting, for moving said closing means to a position permitting said slides to pass through said outlet port.

2. A slide supply device according to claim 1 wherein said closing means is provided on a side face of said cassette.

3. A slide supply device according to claim 1 further comprising:

said slide outlet port is a recess opening;

a support member in said recess opening; and moving means for moving said closing means in said recess opening.

4. A slide supply device comprising:

means for accepting at least one cassette containing a plurality of slides;

a slide outlet port in said at least one cassette;

closing means effective to prevent said plurality of slides from passing through said outlet port;

cooperating means between said cassette and said means for accepting for moving said closing means to a position permitting said slides to pass through said outlet port;

means for accepting at least first and second cassettes;

means for moving said first cassette between first and second positions;

means in said first position for permitting removal of said cassette and replacement thereof;

means in said second position for actuating said cooperating means; and means for locking said means for moving in said second position while slides are supplied from said slide supply device.

5. A slide supply device comprising:

means for accepting at least one cassette containing a plurality of slides;

a slide outlet port in said at least one cassette;

closing means effective to prevent said plurality of slides from passing through said outlet port;

cooperating means, between said cassette and said means for accepting, for moving said closing means to a position permitting said slides to pass through said outlet port;

said means for accepting including a turntable having a plurality of slots;

each of said slots being effective for accepting a one of said at least one cassette;

means for rotating said turntable intermittently;

means for locking said turntable in position;

means for extracting a slide from said at least one cassette and placing it in a one of said slots; and means for detecting the presence of said slide in a one of said slots;

said means for extracting being located beneath said turntable.

6. A slide supply device comprising:

means for accepting at least one cassette;

said at least one cassette containing a plurality of slides;

a slide outlet port in said at least one cassette;

closing means effective to prevent said plurality of slides from passing through said outlet port;

cooperating means, between said cassette and said means for accepting, for moving said closing means to a position permitting said slides to pass through said outlet port;

said slide including a frosted area thereon;

a light source projectable on said frosted area when said slide is present in said at least one cassette;

means for detecting light reflected from said frosted area when said slide is present; and said means for detecting being effective for determining that said at least one cassette is empty when said slide is not present.

7. A cassette for storing a plurality of slides comprising:

a body provided with an interior suitable to house said plurality of slides;

a side face on said body;

a slide outlet port in said side face;

said slide outlet port positioned to allow an individual slide of said plurality of slides to pass through transversely from said cassette;

a closing means with a first open position and a second closed position;

said first open position effective to allow said individual slide to transversely pass through said slide outlet port; and said second closed position effective to prevent said individual slide to transversely pass through said slide outlet port.

8. A cassette according to claim 7, wherein said slide outlet port is a recess opening;

a support member in said recess opening; and moving means for moving said closing means in said recess opening.

* * * * *